United States Patent
Mertz et al.

(10) Patent No.: US 7,354,713 B2
(45) Date of Patent: Apr. 8, 2008

(54) METHOD OF USING ESTROGEN-RELATED RECEPTOR GAMMA (ERRγ) STATUS TO DETERMINE PROGNOSIS AND TREATMENT STRATEGY FOR BREAST CANCER, METHOD OF USING ERRγ AS A THERAPEUTIC TARGET FOR TREATING BREAST CANCER, METHOD OF USING ERRγ TO DIAGNOSE BREAST CANCER, AND METHOD OF USING ERRγ TO IDENTIFY INDIVIDUALS PREDISPOSED TO BREAST CANCER

(75) Inventors: Janet E. Mertz, Madison, WI (US); Eric Anthony Ariazi, Chicago, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 863 days.

(21) Appl. No.: 10/654,253

(22) Filed: Sep. 3, 2003

(65) Prior Publication Data

US 2004/0142490 A1    Jul. 22, 2004

Related U.S. Application Data

(60) Provisional application No. 60/408,400, filed on Sep. 5, 2002.

(51) Int. Cl.
*C12Q 1/68*    (2006.01)
(52) U.S. Cl. .................................................. 435/6
(58) Field of Classification Search .................. None
See application file for complete search history.

(56) References Cited

U.S. PATENT DOCUMENTS 5,298,429 A    3/1994   Evans et al.

OTHER PUBLICATIONS

Greenbaum et al., Genome Biology, 2003, vol. 4 (9), pp. 117.1-117.8.*
Alberts et al. Molecular Biology of the Cell, 3rd Edition, 1994, p. 465.*
Mallampalli et al., Biochem. J. 1996, vol. 38, pp. 333-341.*
Fu et al., EMBO journal, 1996, vol. 15, pp. 4392-4401.*
Giguère, Trends Endo. & Meta., Jul. 2002, 13(5): 220-225.*
Chen, F., Zhang, Q., McDonald, T., Davidoff, M. J., Bailey, W., Bai, C., Liu, Q., and Caskey, C. T. Identification of two hERR2-related novel nuclear receptors utilizing bioinformatics and inverse PCR. Gene, 228: 101-109, 1999.
Coward, P., Lee, D., Hull, M. V., and Lehmann, J. M. 4-Hydroxytamoxifen binds to and deactivates the estrogen-related receptor gamma, Proc Natl Acad Sci U S A, 98: 8880-8884, 2001.
Eudy, J. D., Yao, S., Weston, M. D., Ma-Edmonds, M., Talmadge, C. B., Cheng, J. J., Kimberling, W. J., and Sumegi, J. Isolation of a gene encoding a novel member of the nuclear receptor superfamily from the critical region of Usher syndrome type IIa at 1q41. Genomics, 50: 382-384, 1998.
Greschik, H., Wurtz, J. M., Sanglier, S., Bourguet, W., van Dorsselaer, A., Moras, D., and Renaud, J. P. Structural and functional evidence for ligand-independent transcriptional activation by the estrogen-related receptor 3. Mol Cell, 9: 303-313, 2002.
Heard, D. J., Norby, P. L., Holloway, J., and Vissing, H. Human ERRgamma, a third member of the estrogen receptor-related receptor (ERR) subfamily of orphan nuclear receptors: tissue-specific isoforms are expressed during development and in the adult. Mol Endocrinol, 14: 382-392, 2000.
Lu, D., Kiriyama, Y., Lee, K. Y., and Giguere, V. Transcriptional regulation of the estrogen-inducible pS2 breast cancer marker gene by the ERR family of orphan nuclear receptors. Cancer Res. 61: 6755-6761, 2001.
Tremblay, G. B., Bergeron, D., and Giguere, V. 4-Hydroxytamoxifen is an isoform-specific inhibitor of orphan estrogen-receptor-related (ERR) nuclear receptors beta and gamma. Endocrinology, 142: 4572-4575, 2001.

* cited by examiner

*Primary Examiner*—Christopher Yaen
*Assistant Examiner*—Hong Sang
(74) *Attorney, Agent, or Firm*—Quarles & Brady LLP

(57) ABSTRACT

The present invention provides that ERRγ is both a breast cancer biomarker and a breast cancer treatment target. A high ERRγ level in breast cancer cells indicates good prognosis. A high level of ERRγ in breast tissue suspected of being cancerous is indicative of breast cancer. Analyzing ERRγ status and optionally along with the status of ERα can help breast cancer patients make treatment choices. Furthermore, breast cancer can be treated by decreasing ERRγ activity in breast cancer cells.

6 Claims, 5 Drawing Sheets

SEQUENCE LISTING

```
<160> NUMBER OF SEQ ID NOS: 18

<210> SEQ ID NO 1
<211> LENGTH: 16
<212> TYPE: DNA
<213> ORGANISM: Artificial
<220> FEATURE:
<223> OTHER INFORMATION: synthetic PCR primer

<400> SEQUENCE: 1
ggagggcagg ggtgaa                                                         16

<210> SEQ ID NO 2
<211> LENGTH: 20
<212> TYPE: DNA
<213> ORGANISM: Artificial
<220> FEATURE:
<223> OTHER INFORMATION: synthetic PCR primer

<400> SEQUENCE: 2
ggccaggctg ttcttcttag                                                     20

<210> SEQ ID NO 3
<211> LENGTH: 22
<212> TYPE: DNA
<213> ORGANISM: Artificial
<220> FEATURE:
<223> OTHER INFORMATION: synthetic PCR primer

<400> SEQUENCE: 3
ttcccagcaa tgtcactaac tt                                                  22

<210> SEQ ID NO 4
<211> LENGTH: 19
<212> TYPE: DNA
<213> ORGANISM: Artificial
```

```
<220> FEATURE:
<223> OTHER INFORMATION: synthetic PCR primer

<400> SEQUENCE: 4
ttgaggttcc gcatacaga                                              19

<210> SEQ ID NO 5
<211> LENGTH: 22
<212> TYPE: DNA
<213> ORGANISM: Artificial
<220> FEATURE:
<223> OTHER INFORMATION: synthetic PCR primer

<400> SEQUENCE: 5
gtgaccgttt gggagttgat ga                                          22

<210> SEQ ID NO 6
<211> LENGTH: 19
<212> TYPE: DNA
<213> ORGANISM: Artificial
<220> FEATURE:
<223> OTHER INFORMATION: synthetic PCR primer

<400> SEQUENCE: 6
ggctgaggga ggcgttctc                                              19

<210> SEQ ID NO 7
<211> LENGTH: 21
<212> TYPE: DNA
<213> ORGANISM: Artificial
<220> FEATURE:
<223> OTHER INFORMATION: synthetic PCR primer

<400> SEQUENCE: 7
gggaagaatg gggtcgtcaa a                                           21

<210> SEQ ID NO 8
<211> LENGTH: 21
<212> TYPE: DNA
<213> ORGANISM: Artificial
<220> FEATURE:
<223> OTHER INFORMATION: synthetic PCR primer

<400> SEQUENCE: 8
ctcctccctg gggtgtcaag t                                           21

<210> SEQ ID NO 9
<211> LENGTH: 21
<212> TYPE: DNA
<213> ORGANISM: Artificial
<220> FEATURE:
<223> OTHER INFORMATION: synthetic PCR primer

<400> SEQUENCE: 9
gtggcactca gggagcattt a                                           21

<210> SEQ ID NO 10
<211> LENGTH: 19
<212> TYPE: DNA
<213> ORGANISM: Artificial
<220> FEATURE:
<223> OTHER INFORMATION: synthetic PCR primer

<400> SEQUENCE: 10
tctgggactg gggaaaagg                                              19
```

<210> SEQ ID NO 11
<211> LENGTH: 21
<212> TYPE: DNA
<213> ORGANISM: Artificial
<220> FEATURE:
<223> OTHER INFORMATION: synthetic PCR primer

<400> SEQUENCE: 11
tgccctacag agccccaact a                                              21

<210> SEQ ID NO 12
<211> LENGTH: 21
<212> TYPE: DNA
<213> ORGANISM: Artificial
<220> FEATURE:
<223> OTHER INFORMATION: synthetic PCR primer

<400> SEQUENCE: 12
gcttgcgtag ggtgccatta c                                              21

<210> SEQ ID NO 13
<211> LENGTH: 21
<212> TYPE: DNA
<213> ORGANISM: Artificial
<220> FEATURE:
<223> OTHER INFORMATION: synthetic PCR primer

<400> SEQUENCE: 13
aaagtgctgg cccatttcta t                                              21

<210> SEQ ID NO 14
<211> LENGTH: 19
<212> TYPE: DNA
<213> ORGANISM: Artificial
<220> FEATURE:
<223> OTHER INFORMATION: synthetic PCR primer

<400> SEQUENCE: 14
ccttgcctca gtccatcat                                                 19

<210> SEQ ID NO 15
<211> LENGTH: 16
<212> TYPE: DNA
<213> ORGANISM: Artificial
<220> FEATURE:
<223> OTHER INFORMATION: synthetic PCR primer

<400> SEQUENCE: 15
tgccctacga cgacaa                                                    16

<210> SEQ ID NO 16
<211> LENGTH: 19
<212> TYPE: DNA
<213> ORGANISM: Artificial
<220> FEATURE:
<223> OTHER INFORMATION: synthetic PCR primer

<400> SEQUENCE: 16
actcctcctt ctccacctt                                                 19

<210> SEQ ID NO 17
<211> LENGTH: 19
<212> TYPE: DNA
<213> ORGANISM: Artificial
<220> FEATURE:
<223> OTHER INFORMATION: synthetic PCR primer

```
<400> SEQUENCE: 17
ggccatcaga acggacttg                                              19

<210> SEQ ID NO 18
<211> LENGTH: 20
<212> TYPE: DNA
<213> ORGANISM: Artificial
<220> FEATURE:
<223> OTHER INFORMATION: synthetic PCR primer

<400> SEQUENCE: 18
gcccactacc tcccaggata                                             20
```

METHOD OF USING ESTROGEN-RELATED RECEPTOR GAMMA (ERRγ) STATUS TO DETERMINE PROGNOSIS AND TREATMENT STRATEGY FOR BREAST CANCER, METHOD OF USING ERRγ AS A THERAPEUTIC TARGET FOR TREATING BREAST CANCER, METHOD OF USING ERRγ TO DIAGNOSE BREAST CANCER, AND METHOD OF USING ERRγ TO IDENTIFY INDIVIDUALS PREDISPOSED TO BREAST CANCER

CROSS-REFERENCE TO RELATED APPLICATION

This application claims priority to U.S. provisional application Ser. No. 60/408,400, filed on Sep. 5, 2002.

STATEMENT REGARDING FEDERALLY SPONSORED RESEARCH OR DEVELOPMENT

This invention was made with United States Government support awarded by the following agencies: NIH, Grant Numbers CA22443, P30-CA07175 and T32-CA09681; and U.S. Army Medical Research and Materiel Command Grant DAMD17-99-1-9452 and DAMD17-00-1-0668. The United States has certain rights in this invention.

BACKGROUND OF THE INVENTION

Breast cancer afflicts one in eight women in the United States over their lifetime (1). ERα (NR3A1, (2)) mediates estrogen responsiveness (reviewed in (3)) and plays crucial roles in the etiology of breast cancer (reviewed in (4)). It has been developed into the single most important genetic biomarker and target for breast cancer therapy. ERα is present at detectable levels by ligand-binding and immunohistochemical assays in approximately 75% of clinical breast cancers. Selection of patients with ERα-positive breast tumors increases endocrine-based therapy response rates from about one-third in unselected patients to about one-half in patients with ERα-positive tumors (5). Since expression of PgR is dependent upon ERα activity, further selection of patients with ERα- and PgR-positive tumors enhances the breast cancer hormonal therapy response rate to nearly 80% (5). Although ERβ (NR3A2 (2)) also mediates responses to estrogens (reviewed in (3)), its roles in breast cancer are not as well understood. Reports have linked ERβ expression with low tumor aggressiveness (6) and higher levels of proliferation markers in the absence of ERα (7).

Members of the ErbB family of transmembrane tyrosine kinase receptors have been implicated in the pathogenesis of breast cancer. The members include EGFR (also HER1; ErbB1), ErbB2 (HER2; Neu), ErbB3 (HER3) and ErbB4 (HER4) (reviewed in (8)). ErbB members stimulate signal transduction pathways that involve MAPK. In response to initial binding of EGF-like peptide hormones, ErbB members form homodimers and heterodimers in various combinations to recruit distinct effector proteins (reviewed in (9)). Although ErbB2 has not been demonstrated to interact directly with peptide hormones, it serves as a common regulatory heterodimer subunit with other ligand-bound ErbB members (reviewed in (10, 11)). Unlike the other ErbB members, ErbB3 lacks intrinsic kinase activity and, therefore, is required to heterodimerize with other ErbB members to participate in signaling (12).

Independent overexpression of either EGFR (reviewed in (13)) or ErbB2 (reviewed in (14)) associates with ER-negative tumor status, indicates aggressive tumor behavior, and predicts poor prognosis. Moreover, patients whose tumors coexpress both EGFR and ErbB2 exhibit a worse outcome than patients with tumors that overexpress only one of these genes (15, 16). Overexpression of ErbB2, most often due to gene amplification, occurs in approximately 15-30% of all breast cancers ((17), reviewed in (14)). Some (18-23), but not all reports (24, 25), have implicated ErbB2 in the development of resistance to antiestrogens.

ErbB2 has been targeted for development of the successful clinical agent Herceptin (trastuzumab), a recombinant humanized monoclonal antibody directed against this receptor's ectodomain (reviewed in (26)). Herceptin has been shown to be a suitable option as a first-line single-agent therapy (27), but will likely prove most beneficial as an adjuvant (28, 29). Clinical trials are currently underway to evaluate the combination of Herceptin with antiestrogens as a rational approach to treating ERα-positive/ErbB2-overexpressing tumors (23). In the near future, Herceptin will also likely be evaluated in combination with the small molecule EGFR tyrosine kinase inhibitor ZD 1829 (Iressa), since this ATP-mimetic has been shown to almost completely block transphosphorylation of ErbB2 via heterodimerization with EGFR in intact cells (30) and inhibits the growth of breast cancer cell lines overexpressing both EGFR and ErbB2 (31). Hence, a combination of ZD1829 and Herceptin may be particularly beneficial to those patients whose tumors coexpress EGFR and ErbB2.

The ability of ErbB3 and ErbB4 to predict clinical course is not as clearly recognized as that of EGFR and ErbB2. ErbB3 has been observed at higher levels in breast tumors than normal tissues, showing associations with unfavorable prognostic indicators including ErbB2 expression (32), lymph node-positive status (33), and tumor size. However, it also associated with ERα-positive status, a favorable marker of hormonal sensitivity (34). In contrast, ErbB4 has shown associations with only positive indicators. ErbB4 overexpression has been associated with ERα-positive status (34, 35), more differentiated histotypes (36), a more favorable outcome (16) and it may oppose the negative effects of ErbB2 on clinical course (16).

Despite the utility of ERs and ErbB members as indicators of clinical course, there remains a great need to identify additional breast cancer biomarkers. A family of potential candidate biomarkers includes the orphan nuclear receptors ERRα (37-39), ERRβ (37, 40), and ERRγ (40-42) (NR3B1, NR3B2, and NR3B3, respectively (2)). These receptors share significant amino acid sequence identity with ERα and ERβ. They also exhibit similar but distinct biochemical and transcriptional activities as the ERs. Each of the ERRs has been demonstrated to bind and activate transcription via consensus palindromic EREs (43-46) in addition to ERREs (39, 42, 44, 47-50), which are composed of an ERE half-site with a 5' extension of 3 base pairs. However, whereas ERs are ligand-activated transcription factors, the ERRs do not bind natural estrogens (37, 51). Instead, the ERRs may serve as constitutive regulators, interacting with transcriptional coactivators in vitro in the absence of ligands (45, 50, 52). Bulky amino acid side chains in the ligand binding pockets of ERRs substitute for the analogous ligand-induced interactions observed in ERα (52, 53). However, the ligand-binding pockets of the ERRs still allow binding of the synthetic estrogen diethylstilbestrol, but as an antagonist because it also disrupts coactivator interactions with ERRs (51). Similarly, the selective estrogen receptor modulator (SERM) 4-hydroxytamoxifen selectively antagonizes ERRγ in cell-based assays (46, 52, 54).

The transcriptional activity of each ERR depends upon the promoter and the particular cell line in which it is assayed as well as the presence of ERs. (42-46, 48-51, 53-62) For example, whereas ERRα stimulates ERE-dependent transcription in the absence of ERα in HeLa cells, it down-modulates $E_2$-stimulated transcription in ERα-positive human mammary carcinoma MCF-7 cells via an active mechanism of repression. (43) ERRα can also modulate transcription of at least some genes that are estrogen responsive and/or implicated in breast cancer such as pS2 (55), aromatase (59), osteopontin (57, 58) and lactoferrin (56, 61). Thus, the ERRs likely play important roles in at least some breast cancers by modulating or substituting for ER-dependent activities.

BRIEF SUMMARY OF THE INVENTION

The present invention discloses that ERRγ is both a breast cancer biomarker and a breast cancer treatment target. In one embodiment, the present invention is a method of determining prognosis of breast cancer by determining the level of ERRγ in the breast cancer cells. A low level of ERRγ indicates a poor prognosis and a high level of ERRγ indicates a good prognosis.

In another embodiment, the present invention is a method of categorizing breast cancer patients for treatment purposes by determining the status of ERRγ either alone or in conjunction with ERα and/or ErbB4 in breast cancer cells.

In another embodiment, the present invention is a method of determining whether an individual is at increased risk or predisposed to developing breast cancer by screening for overexpression and/or mutations in the ERRγ gene.

In another embodiment, the present invention is a method to assist in diagnosing breast cancer by measuring ERRγ expression in the breast cells which are suspected of being cancerous.

In another embodiment, the present invention is a method of treating breast cancer by decreasing ERRγ activity.

It is an object of the present invention to identify more biomarkers and treatment targets for breast cancer.

It is an advantage of the present invention that the biomarker identified helps diagnose, predict prognosis and select treatment strategies for breast cancer.

Other objects, advantages, and features of the present invention will become apparent from the following detailed description of the invention.

DETAILED DESCRIPTION OF THE INVENTION

Figure 1:
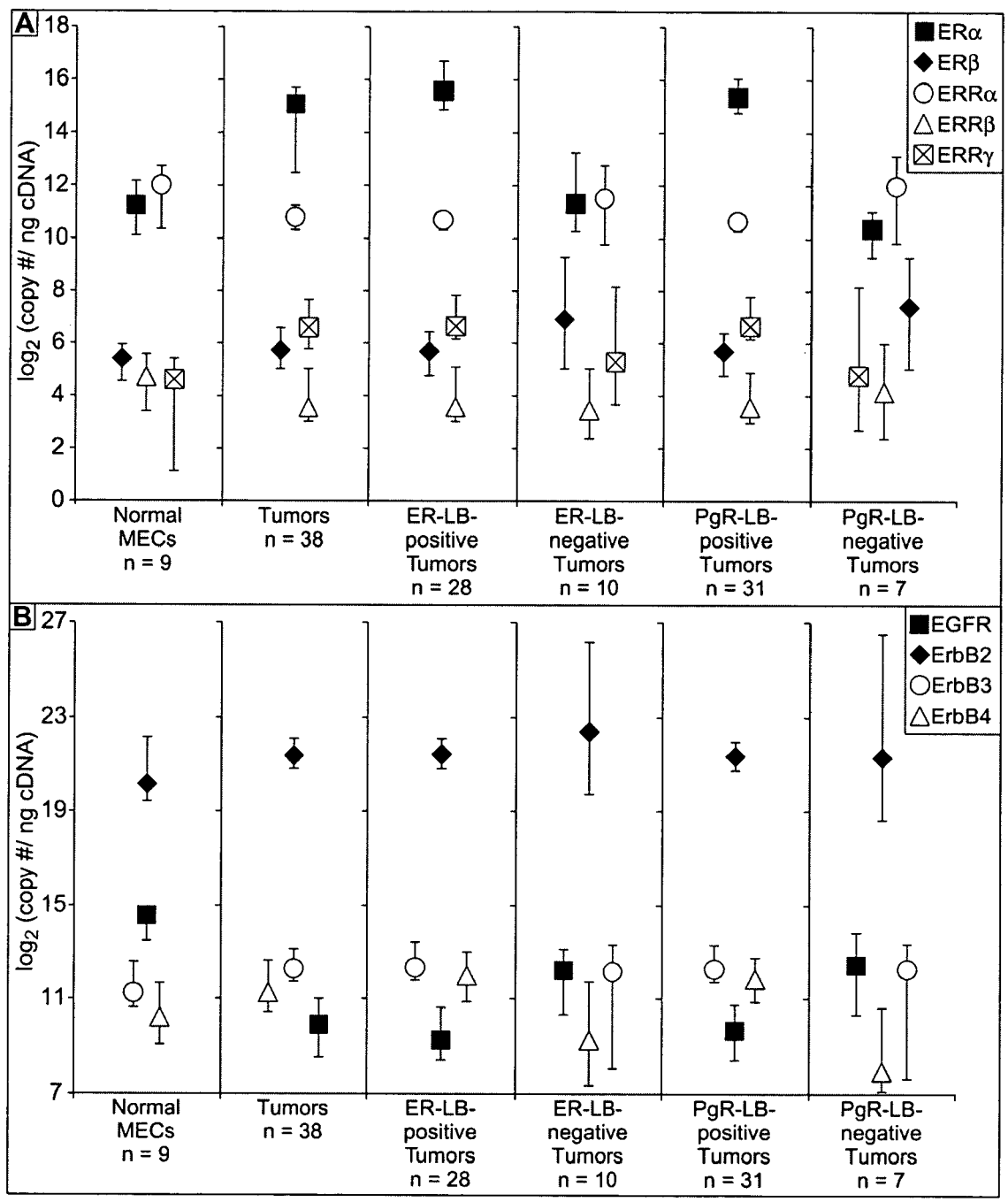
FIG. 1 shows gene expression distributions of ER and ERR family members (A) and ErbB family members (B). Expression levels are depicted as the 95% confidence intervals of the medians of $\log_2$-transformed values.

The Example below shows that in breast cancer cells, high ERRγ levels associate with ER-LB-positive and PgR-LB-positive status and with DNA diploid status. In breast cancer cells, ERRγ levels also associate with levels of the positive prognosis indicator ErbB4. Thus, ERRγ can be a biomarker for prognosis and for sensitivity to hormonal blockade therapy (such as tamoxifen therapy) in that high levels of ERRγ indicates good prognosis and high likelihood of being sensitive to hormonal blockade therapy. The Example below also shows that breast cancer cells have higher ERRγ levels than normal mammary epithelial cells indicating that ERRγ plays a role in breast cancer development. Thus, ERRγ may serve as a diagnostic marker and a treatment target. Furthermore, overexpression of ERRγ or mutations in ERRγ may predispose a human being for breast cancer development. Therefore, screening for ERRγ overexpression and mutations may help identify individuals for further breast cancer examination. Without intending to be limited by theory, we believe that high levels of ERRγ can lead to the development of breast cancer, but breast cancer with a high level of ERRγ has a good prognosis because it is likely sensitive to hormonal blockade therapy.

In the specification and claims, the term "status" of ERRγ, ERα and ErbB4 refers to the "expression status" of the genes. The status can be determined either at the mRNA level or at the protein level, and either qualitatively (expressed or not expressed) or quantitatively (the level of expression). There are many methods known to a skilled artisan that can be used in the present invention to determine the status of ERRγ and ERα. As an example, the status of ERα was determined by the ligand binding assays in the Example below.

In one aspect, the present invention is a method for determining breast cancer prognosis by analyzing the status of ERRγ in the breast cancer tissue. A high ERRγ level in breast cancer cells indicates good prognosis and a low ERRγ level in breast cancer cells indicates poor prognosis. This means that after diagnosis, breast cancer patients with a high ERRγ level have a greater likelihood of responding to treatment such as hormonal blockade than those with low ERRγ levels. As used in the specification and claims, a high or low level of ERRγ in breast cancer cells is measured against a median level of ERRγ obtained from breast cancer tissues of multiple patients. The more the breast cancer tissue samples of different breast cancer patients are used to establish the median level, the more accurate the median level is. Preferably, the median level is obtained from analyzing breast cancer tissues of at least 25 patients. The high or low level of ERRγ in breast cancer cells can also be measured against the median or average level of ERRγ in normal breast cells obtained from multiple human subjects. Preferably, normal breast cells of at least 25 human subjects are used to establish the median or average level of ERRγ. The high or low level of ERRγ in breast cancer cells can also be measured against other standards that a skilled artisan can readily establish. For example, ERRγ levels of normal breast epithelial cell lines and breast cancer cell lines can be used as standards.

In another aspect, the present invention is a method for categorizing breast cancer patients for treatment purposes. The method involves determining the status of ERRγ in breast cancer cells. Because 4-OH tamoxifen is an antagonist of ERRγ, if the breast cancer cells of a patient exhibit high levels of ERRγ, the patient has a greater likelihood of responding to tamoxifen therapy. Tamoxifen therapy should be provided to such a patient.

In a preferred embodiment of a method of categorizing breast cancer patients for treatment purposes, the ERRγ status is determined in conjunction with ERα status. If the breast cancer cells of a patient are ERα-positive and exhibit high levels of ERRγ, the patient is likely to respond to hormonal blockade therapy. Hormonal blockade therapy includes the use of anti-estrogens, aromatase inhibitors and other agents that can block the production or activity of estrogen.

If the breast cancer cells of a patient are ERα-positive and exhibit low levels of ERRγ, the patient may still respond to hormonal blockade therapy but the likelihood is less than those patients who have ERα-positive cancers that also exhibit a high level of ERRγ expression. Thus, hormonal blockade therapy remains an option for patients with ERα-positive and low level ERRγ cancers. However, other therapies should be considered as well for these patients.

If the breast cancer cells of a patient are ERα-negative and have high levels of ERRγ, the patient may still respond to tamoxifen, although the likelihood is less than those patients who have ERα-positive cancers that also exhibit a high level of ERRγ expression. The reason that such a patient may respond to hormonal blockade therapy is that the antiestrogen 4-hydroxytamoxifen binds to and antagonizes the activity of ERRγ. Therefore, a high level of ERRγ expression in cancers of patients that are also ERα-negative identifies a subset of patients that may benefit from tamoxifen therapy, but otherwise would not have been good candidates for tamoxifen therapy. Nonetheless, while tamoxifen therapy remains an option for patients with ERα-negative cancers that also exhibit a high level of ERRγ expression, other breast cancer therapies should be considered as well.

If the breast cancer cells of a patient are ERα-negative and have low levels of ERRγ, the patient is not likely to respond to hormonal blockade therapy. Other breast cancer therapies should be provided for the patient.

In another embodiment of a method of categorizing breast cancer patients for treatment purposes, the ERRγ status is determined in conjunction with ErbB4 status. In the Example described below, ERRγ levels in breast cancer cells correlate with ErbB4 levels. We hypothesize that ERRγ is a downstream target of ErbB4 signal transduction. By analogy with ErbB2, there is the potential that anti-tumor agents will be developed that target ErbB4. For instance, the anti-ErbB2 monoclonal antibody Herceptin has been developed and is currently in use in the clinic as a therapeutic agent. ErbB4-based therapy includes the use of agents that either directly inhibit ErbB4 activity (anti-ErbB4 antibodies and ErbB4-specific kinase inhibitors) or indirectly inhibit ErbB4 activity through heterodimerization with other ErbB members. If ErbB4-based therapies are developed for the treatment of breast cancer, when the breast cancer cells of a patient have a high ErbB4 level and a high ERRγ level, the patient is likely to respond to the ErbB4-based therapy. When the breast cancer cells of a patient have a high ErbB4 level and a low ERRγ level, the patient is less likely to respond to ErbB4-based therapy. However, breast cancer therapies other than ErbB4-based therapy and hormonal blockade therapy should be seriously considered as well.

In another aspect, the present invention is a method for diagnosing breast cancer by measuring the ERRγ level in the suspected or abnormal breast cells and comparing it to a reference normal level. If someone has a lump or a locus in a breast that is suspected of being breast cancer, cells from the lump or locus can be taken and the ERRγ level can be measured. The reference normal level to which the measured ERRγ level is compared can be obtained from several sources. For example, the reference normal level can be the ERRγ level of normal mammary epithelial cells obtained from the same human subject at the time the sample from the suspected lump or locus was taken; the reference normal level can also be the ERRγ level of normal mammary epithelial cells obtained from the same human subject during a breast cancer-free period; the reference normal level can also be a normal range of ERRγ levels determined by analyzing a large number of normal breast tissue samples from multiple human subjects. Finding that the cells from the lump or locus exhibit an ERRγ level higher than the reference normal level is indicative of the tissue in question being cancerous. In a preferred embodiment, the ERRγ level is used in combination with other breast cancer diagnostic tools such as pathological analysis of suspected tissue to diagnose breast cancer.

In another aspect, the present invention is a method of treating breast cancer by decreasing ERRγ activity. For example, an antisense oligonucleotide or small inhibitor RNA (siRNA) targeted against ERRγ can be used to inhibit the RNA expression of ERRγ. Other agents that can decrease ERRγ expression can be identified by exposing a group of cells that express ERRγ to a test agent and comparing the ERRγ expression of these cells at the mRNA level or at the protein level to that of control cells that are not exposed to the agent.

One can also use an ERRγ antagonist to decrease ERRγ activity. 4-hydroxytamoxifen is an ERRγ antagonist. Other ERRγ antagonists can be identified by exposing ERRγ to a test agent and determining whether the test agent binds to ERRγ. There are many ways that this can be done. For example, a test agent can be labeled and ERRγ can be exposed to the test agent, washed and purified. If the label is detected with the purified ERRγ, then the test agent has bound to ERRγ. Once a test agent is determined to be capable of binding ERRγ, whether the agent can inhibit ERRγ activity can be determined. For example, a reporter gene for ERRγ activity with and without an ERRγ expression plasmid can be introduced into a cell. The cell can then be exposed to the agent and the reporter gene expression levels in the absence and presence of overexpressed ERRγ can be determined.

In a more general manner, a cell culture reporter gene assay for ERRγ can be used directly to screen for agents that can decrease ERRγ activity by exposing the cells to a test agent and determining the reporter gene expression levels in the absence and presence of overexpressed ERRγ.

ERRγ activity can also be inhibited by an ERRγ antibody (either monoclonal or polyclonal), which can be readily generated by a skilled artisan. Encapsulating liposomes or other similar technology can be used to deliver anti-ERRγ antibodies into cells. Alternatively, recombinant DNAs expressing an anti-ERRγ antibody (such as in the form of a single-chain antibody fragment) can be introduced into cells via gene therapy methodologies.

In another aspect, the present invention is a method of identifying an individual for further breast cancer examination by screening the individual for overexpression of the ERRγ gene, for mutations in the ERRγ gene, or for both. An individual who overexpresses or carries a mutated ERRγ gene should be monitored closely for breast cancer development. Whether ERRγ is overexpressed can be determined using a reference normal level described above. Whether a mutation exists in the ERRγ gene is determined using a reference ERRγ sequence. For example, the National Center for Biotechnology Information (NCBI) Reference Sequence entry for ERRγ, NM_001438, can be used as a reference ERRγ sequence. An individual who overexpresses or carries a mutated ERRγ gene should be monitored closely for breast cancer development.

The invention will be more fully understood upon consideration of the following non-limiting example.

EXAMPLE

Estrogen-related Receptor α and Estrogen-related Receptor γ Associate with Unfavorable and Favorable Biomarkers, Respectively, in Human Breast Cancer Abstract The importance of estrogen-related receptors (ERRs) in human breast cancer was assessed by comparing their mRNA profiles with established clinicopathologic indicators and mRNA profiles of estrogen receptors (ERs) and ErbB family members. Using real-time quantitative polymerase chain reaction assays, mRNA levels of ERα, ERβ, EGFR (epidermal growth factor receptor), ErbB2, ErbB3, ErbB4, ERRα, ERRβ, and ERRγ were determined in unselected primary breast tumors (n=38) and normal mammary epithelial cells (MECs) enriched from reduction mammoplasties (n=9). ERRα was shown to be a biomarker of unfavorable clinical outcome and hormonal insensitivity. ERRα mRNA was expressed at levels greater than or similar to ERα mRNA in 24% of unselected breast tumors, and generally at higher levels than ERα in the PgR-negative tumor subgroup (1-way ANOVA with repeated measures, P=0.030). Increased ERRα levels associated with ER-negative (Fisher's exact, P=0.003) and PgR-negative tumor status (Fisher's exact, P=0.006; Kruskal-Wallis ANOVA, P=0.021). ERRα levels also correlated with expression of ErbB2 (Spearman's rho, P=0.005), an indicator of aggressive tumor behavior. Thus, ERRα was the most abundant nuclear receptor in a subset of tumors that tended to lack functional ERα and expressed ErbB2 at high levels. Consequently, ERRα may potentiate constitutive transcription of estrogen response element-containing genes independently of ERα and antiestrogens in ErbB2-positive tumors. ERRβ's potential as a biomarker remains unclear: it showed a direct relationship with ERβ (Spearman's rho, P=0.0002) and an inverse correlation with S-phase fraction (Spearman's rho, P=0.026). Unlike ERRα, ERRγ was shown to be a biomarker of favorable clinical course and hormonal sensitivity. ERRγ was overexpressed in 75% of the tumors, resulting in the median ERRγ level being elevated in breast tumors compared to normal MECs (Kruskal-Wallis ANOVA, P=0.001). ERRγ overexpression associated with hormonally responsive ER- and PgR-positive status (Fisher's exact, P=0.054 and P=0.045, respectively). Additionally, ERRγ expression correlated with levels of ErbB4 (Spearman's rho, P=0.052), a likely indicator of preferred clinical course, and associated with diploid-typed tumors (Fisher's exact, P=0.042). Hence, ERRα and ERRγ status can be predictive of sensitivity to hormonal blockade therapy, and ERRα status can also be predictive of ErbB2-based therapy such as Herceptin. Moreover, ERRα and ERRγ are targets for therapeutic development.

Materials and Methods

Tissue Sources: Random primary breast cancer samples were obtained from the National Breast Cancer Tissue Resource SPORE at Baylor College of Medicine (Houston, Tex.). Records of previously determined clinicopathologic tumor biomarkers were maintained at the SPORE, including ER-LB (ligand binding) and PgR-LB protein levels measured by the ligand-binding assay, and S-phase fraction and DNA ploidy determined by flow cytometry. The mRNA profiling studies were conducted in a blinded manner regarding these previously determined biomarkers.

As a basis of comparison, mammary gland tissues were also profiled for mRNA expression. Because bulk mammary gland contains overwhelming amounts of adipose, it was necessary to enrich for epithelial cells prior to isolation of nucleic acid. Hence, mammary tissues from reduction mammoplasties were processed through collagenase digestion and differential centrifugation and filtration steps. These enriched MECs were kindly provided by Dr. Stephen Ethier (University of Michigan-Ann Arbor) and Dr. Michael N. Gould (University of Wisconsin-Madison). The normal MECs used here were not expanded in culture to avoid any possible changes in RNA profiles that might occur with passage. All use of human tissues was approved by the University of Wisconsin's Human Subjects Committee.

Real-time Q-PCR Assays: The mRNA abundances of ER, ErbB and ERR family members were determined by real-time Q-PCR assays. As detailed below, amplification of PCR products was continuously monitored by fluorescence facilitated by specific complex formation of SYBR Green I with double-stranded DNA (reviewed in (63)).

Total RNA was isolated from tissues using the Total RNeasy kit (Qiagen; Valencia, Calif.), treated with RNase-free DNase I (Ambion; Austin, Tex.), and again purified with the Total RNeasy kit. cDNA was synthesized by incubation of 10 µg total RNA with SuperScript II reverse transcriptase (Invitrogen Life Technologies; Carlsbad, Calif.) and 50 nmoles each of oligo $dT_{15}VN$ (where V=A, G, or C and N=any nucleotide) and random hexamers as primers in a total reaction volume of 100 µl at 45° C. for 1 h. Because the quality of the mRNA purified from the tumors likely varied considerably, differences in mRNA integrity were compensated for by careful quantitation by trace radiolabel incorporation of the amount of cDNA synthesized from each sample followed by use of the same amount of cDNA in each Q-PCR assay. Quantitation of cDNA involved trace radiolabeling of a parallel cDNA synthesis reaction carried out in the presence of [$\alpha$-$^{32}$P]dCTP. Incorporated and total radiolabeled amounts were measured in triplicate by trichloroacetic acid precipitation and scintillation counting. Calculation of the total mass of cDNA synthesized was based upon the molar amount of nucleotides present in the reaction converted to mass and multiplied by the ratio of incorporated-to-total radiolabel. Q-PCR assays involving tissue samples employed 1 ng cDNA as template and were carried out in triplicate.

PCR primer sets were designed to promote efficient amplification by yielding products smaller than 150 bp in length. PCR products were verified by sequence analysis. The PCR primer set sequences and amplicon sizes were as follows: ER$\alpha$ forward primer 5'-GGAGGGCAGGGGT-GAA-3' (SEQ ID NO:1) and reverse primer 5'-GGCCAG-GCTGTTCTTCTTAG-3' (SEQ ID NO:2), 100-bp amplicon; ER$\beta$ forward primer 5'-TTCCCAGCAATGTCACTAACTT-3' (SEQ ID NO:3) and reverse primer 5'-TTGAGGTTCCGCATACAGA-3' (SEQ ID NO:4), 137-bp amplicon; EGFR forward primer 5'-GTGACCGTTTGGGAGTTGATGA-3' (SEQ ID NO:5) and reverse primer 5'-GGCTGAGGGAGGCGTTCTC-3' (SEQ ID NO:6), 104-bp amplicon; ErbB2 forward primer 5'-GGGAAGAATGGGGTCGTCAAA-3' (SEQ ID NO:7) and reverse primer 5'-CTCCTCCCTGGGGTGTCAAGT-3' (SEQ ID NO:8), 82-bp amplicon; ErbB3 forward primer 5'-GTGGCACTCAGGGAGCATTTA-3' (SEQ ID NO:9) and reverse primer 5'-TCTGGGACTGGGGAAAAGG-3' (SEQ ID NO:10), 106-bp amplicon; ErbB4 forward primer 5'-TGCCCTACAGAGCCCCAACTA-3' (SEQ ID NO:11) and reverse primer 5'-GCTTGCGTAGGGTGCCATTAC-3' (SEQ ID NO:12), 105-bp amplicon; ERR$\alpha$ forward primer 5'-AAAGTGCTGGCCCATTTCTAT-3' (SEQ ID NO:13) and reverse primer 5'-CCTTGCCTCAGTCCATCAT-3' (SEQ ID NO:14), 100-bp amplicon; ERR$\beta$ forward primer 5'-TGCCCTACGACGACAA-3' (SEQ ID NO:15) and reverse primer 5'-ACTCCTCCTTCTCCACCTT-3' (SEQ ID NO:16), 144-bp amplicon; and ERR$\gamma$ forward primer 5'-GGCCATCAGAACGGACTTG-3' (SEQ ID NO:17) and reverse primer 5'-GCCCACTACCTCCCAGGATA-3' (SEQ ID NO:18), 67-bp amplicon. PCR primer sequences were designed using Oligo 5.0 software (National Biosciences; Plymouth, Minn.) and synthesized at the University of Wisconsin-Biotechnology Center (Madison, Wis.).

Serial dilution standard curves of each specific PCR product were included in every experiment and allowed calculation of transcript copy numbers in the unknown samples by regression analysis. The PCR product standards were in the form of ssDNA to better emulate cDNA in the unknown samples. The ssDNA standards were produced by linear amplification, using only the reverse primer (corresponding to the non-coding DNA strand), instead of by exponential amplification with two primers. The amount of each template required for the standard curves was determined in a similar manner as described above by trace radiolabeling with [$\alpha$-$^{32}$P]dCTP incorporation during the PCR amplification process. The mass of PCR product synthesized was converted to copy numbers according to the molecular weight of the specific amplicon's size in base pairs. All standard curves covered eight orders-of-magnitude and were assayed in triplicate.

Q-PCR assays were carried out in a total volume of 20 µl with 10 µl of 0.1 ng/µl cDNA. SYBR Green I (Molecular Probes; Eugene, Oreg.) was diluted in anhydrous DMSO at 1:2,500, then added to the enzyme reaction buffer to obtain a final concentration of 1:50,000 SYBR green I and 5% DMSO. To normalize fluorescence intensity between samples, the enzyme reaction buffer contained 180 nM passive reference dye ROX (Molecular Probes). The final concentrations of the remaining constituents were as follows: 10 mM Tris-HCl (pH 8.3), 50 mM KCl, 2.5 mM $MgCl_2$, 50 µM each dNTP, 500 nM each forward and reverse primer, and 0.025 units per µl HotStar Taq DNA polymerase (Qiagen). The thermal cycling parameters were 1 cycle of 95° C. for 10 min, and 40 cycles of 96° C. denaturation for 15 s followed by 60° C. annealing/extension for 1 min. Q-PCR assays were carried out with an ABI 7700 sequence detection system (Applied Biosystems, Foster City, Calif.).

ER and PgR by Ligand-binding Assays: ER and PgR content of the breast tumors were previously determined in a central laboratory. The standard multipoint, dextran-coated charcoal assay was modified as previously described (64) to incorporate $^{125}$I-labeled estradiol and $^3$H-labeled R5020 in a single assay, allowing the simultaneous determination of both ER and PgR. ER-LB levels greater than or equal to 3 fmol/mg protein were considered positive, and PgR-LB levels greater than or equal to 5 fmol/mg protein were considered positive.

DNA Ploidy and S-phase Fraction by Flow Cytometry: Flow cytometry was performed as previously described to determine DNA ploidy and S-phase fraction (64, 65). S-phase fractions were estimated using the MODFIT program (Verity House Software, Inc., Topsham, Me.). S-phase fractions less than 6% were considered low; S-phase fractions greater than 10% were considered high; and values between 6 and 10% were considered intermediate.

Figure 2:
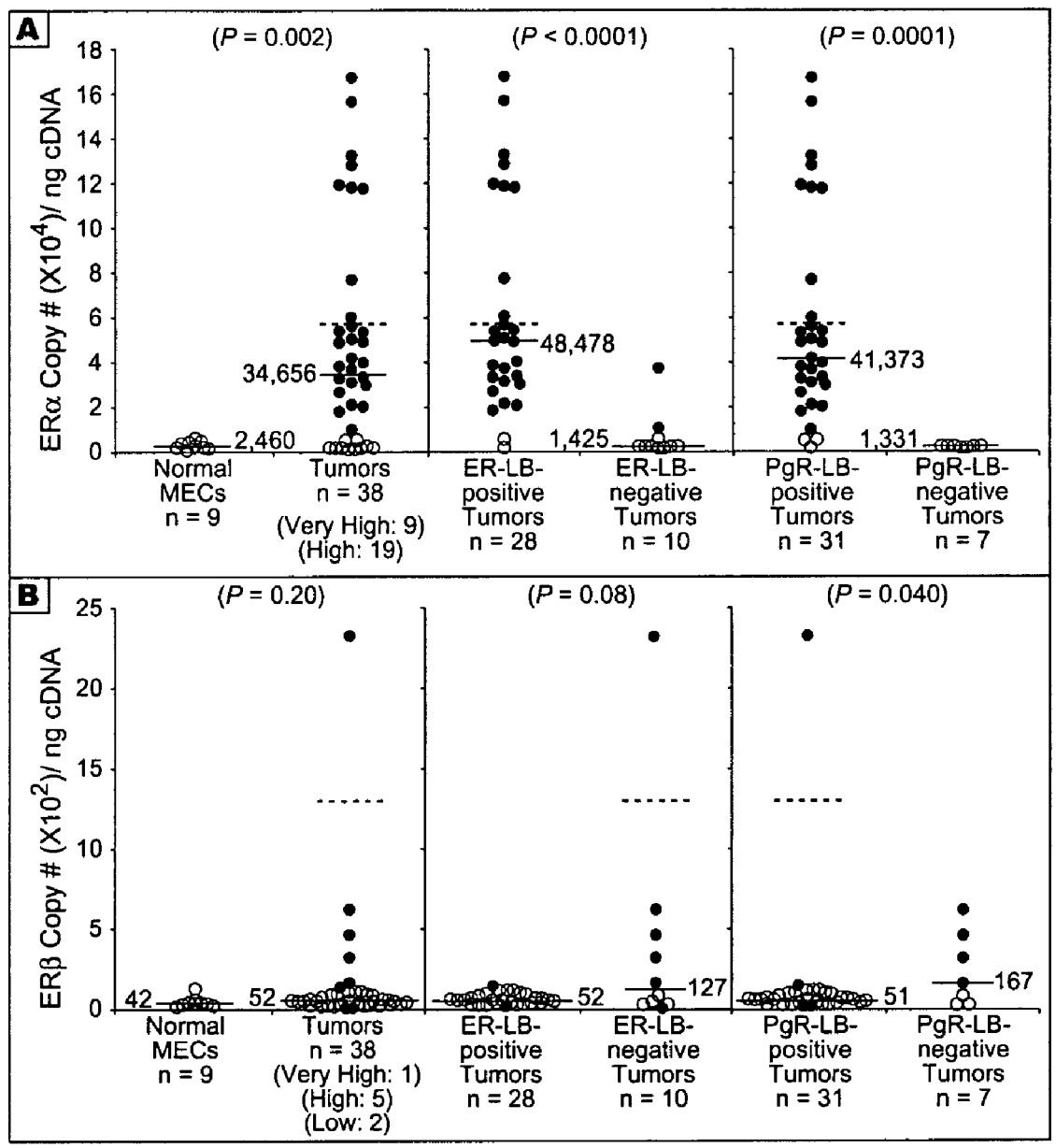
FIG. 2 shows ER family member mRNA levels (A for ERα levels and B for ERβ levels) in normal MECs, breast tumors, and tumors segregated by ER-LB and PgR-LB status. The numbered solid horizontal bars indicate the median level within each group. The dashed horizontal bars in the tumor groups indicate the level 10-fold above the upper limit of the range of expression for the normal MECs. The solid symbols indicate tumors expressing mRNA at levels greater or less than the entire range of expression observed in the normal MECs. Statistical significance was determined by the non-parametric Kruskal-Wallis ANOVA.
Figure 3:
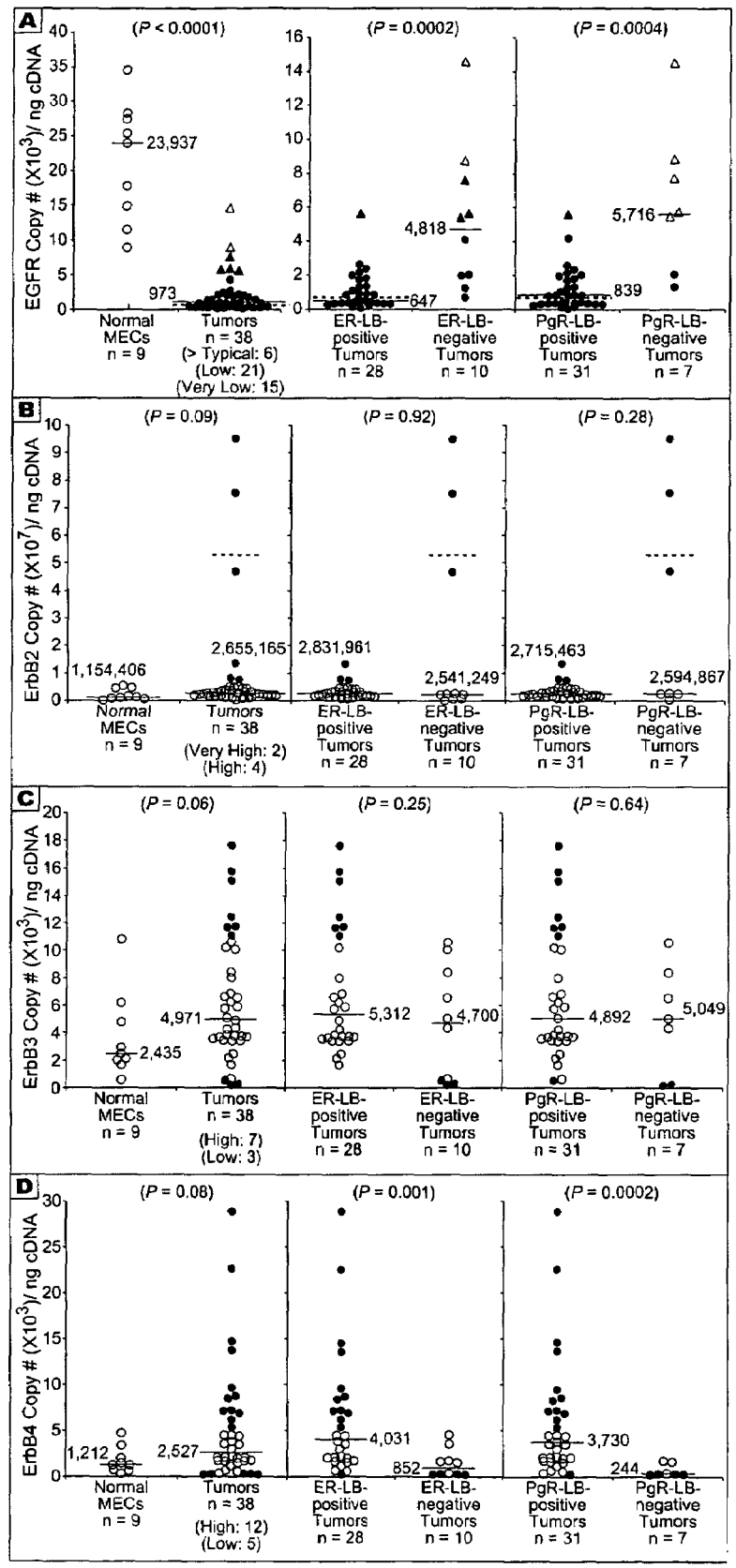
FIG. 3 shows ErbB family member mRNA levels (A for EGFR levels, B for ErbB2 levels, C for ErbB3 levels and D for ErbB4 levels) in normal MECs, breast tumors, and tumors segregated by ER-LB and PgR-LB status. Note the different scales used within (A). The numbered solid horizontal bars indicate the median level within each group. The dashed horizontal bars in the tumor groups indicate the level 10-fold above or below the upper or lower limit, respectively, of the range of expression for the normal MECs. The solid symbols indicate tumors expressing mRNA at levels greater or less than the entire range of expression observed in the normal MECs. Triangles in (A) indicate tumors expressing EGFR mRNA at levels greater or less than one standard deviation surrounding the mean for the tumor group. Statistical significance was determined by the non-parametric Kruskal-Wallis ANOVA.
Figure 4:
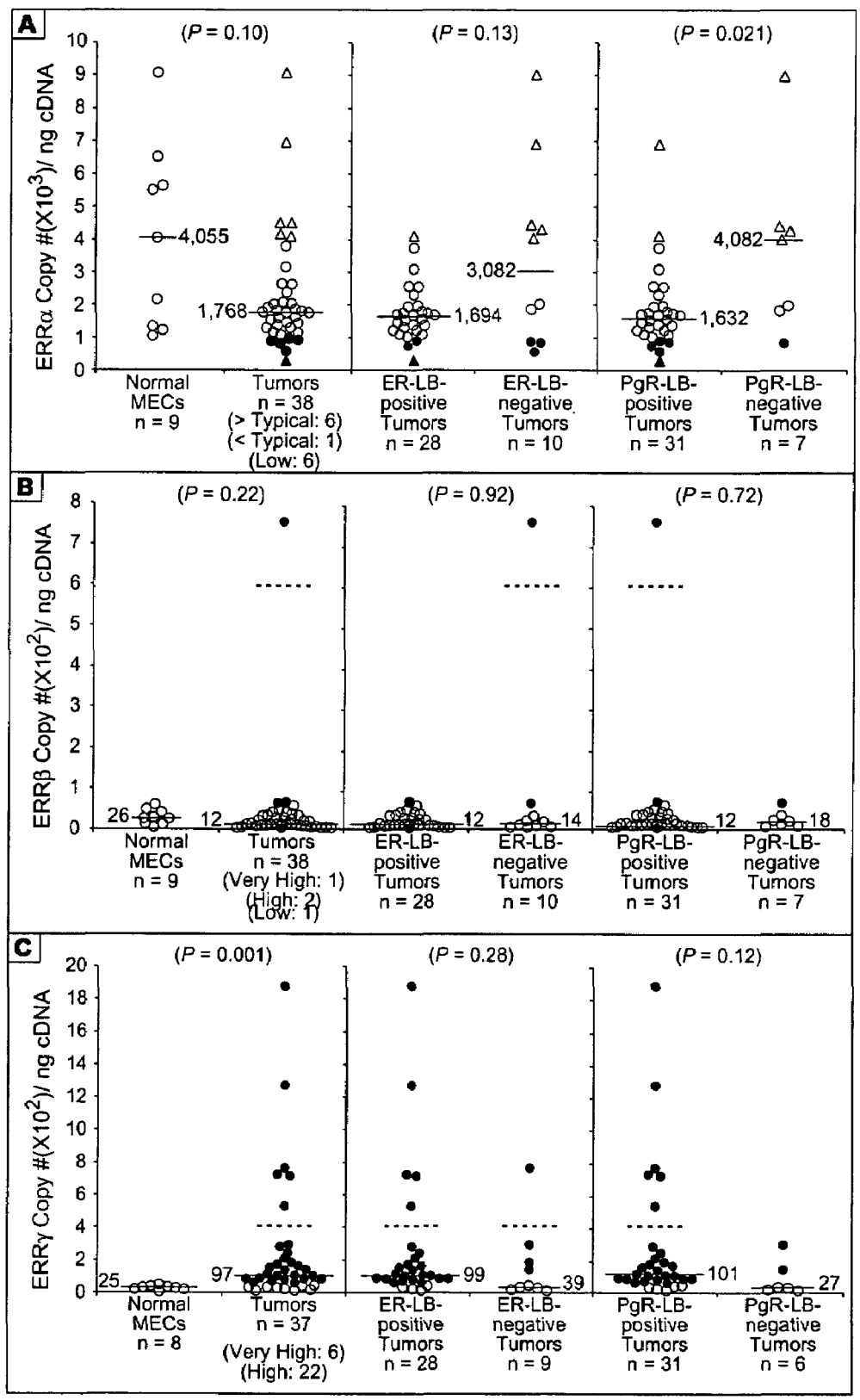
FIG. 4 shows ERR family member mRNA levels (A for ERRα levels, B for ERRβ levels and C for ERRγ levels) in normal MECs, breast tumors, and tumors segregated by ER-LB and PgR-LB status. The numbered solid horizontal bars indicate the median level within each group. The dashed horizontal bars in the tumor groups indicate the level 10-fold above or below the upper or lower limit, respectively, of the range of expression for the normal MECs. The solid symbols indicate tumors expressing mRNA at levels greater or less than the entire range of expression observed in the normal MECs. Triangles in (A) indicate tumors expressing ERRα mRNA at levels greater or less than one standard deviation surrounding the mean for the tumor group. Statistical significance was determined by the non-parametric Kruskal-Wallis ANOVA.
Figure 5:
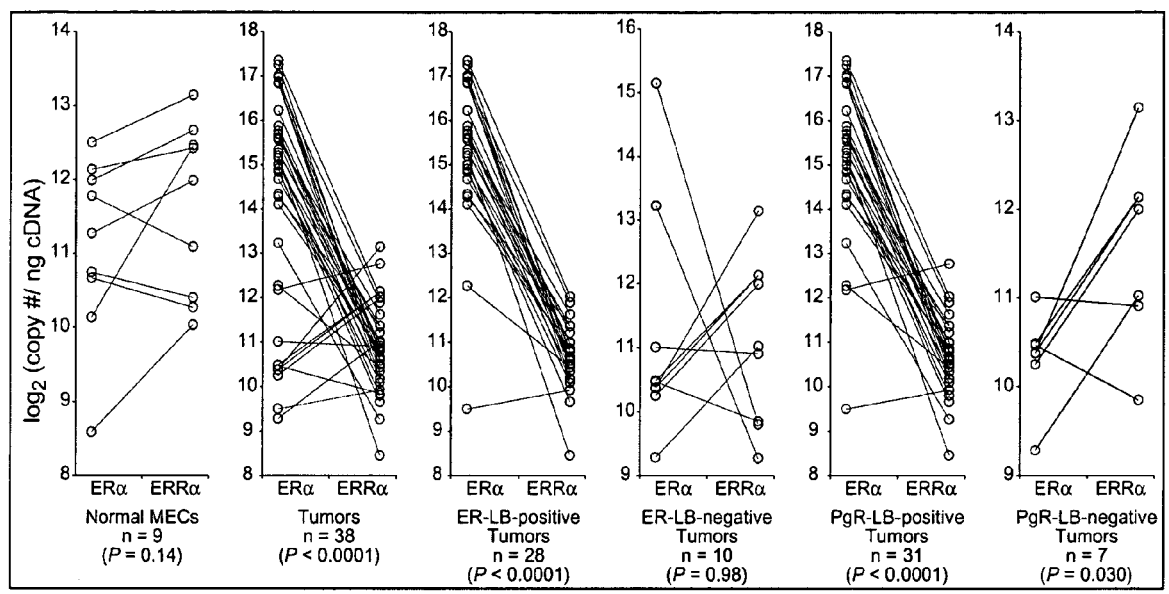
FIG. 5 shows ERα and ERRα mRNA levels within the same tissue sample. Significance was assessed by 1-way ANOVA with repeated measures on $\log_2$-transformed values.

Statistics: Differences in abundance among separate mRNA species grouped by biological function were evaluated as independent variables using the 95% confidence intervals of the medians of $log_2$-transformed values (FIG. 1). Changes in the abundance of a single mRNA species between tissue groups were tested by the non-parametric Kruskal-Wallis ANOVA (FIG. 2, FIG. 3, and FIG. 4). Associations between aberrant mRNA levels and clinicopathological biomarkers in the breast tumors were evaluated by Fisher's exact tests (Table 1). To analyze aberrant tumor expression relative to MECs, high and low expression in the breast tumors was defined as mRNA levels above or below, respectively, the range of expression in the normal MECs. Similarly, very high and very low expression in the tumors was defined as 10-fold above or below, respectively, the range of expression in normal MECs. Additionally, to analyze aberrant tumor expression relative to only other tumors and not MECs in the cases of EGFR and ERR$\alpha$, typical expression was defined as being within a standard deviation and aberrant expression as greater than a standard deviation away from the mean tumor level. Differences in expression between ER$\alpha$ and ERR$\alpha$ mRNA levels within the same tissue sample were assessed by 1-way ANOVA with repeated measures on $log_2$-transformed data (FIG. 5). To discern whether ER$\alpha$ and ERR$\alpha$ were expressed at approximately equivalent levels within tumors, the ratio of their levels was stratified according to those found in normal MECs; ratios within a standard deviation of the average ratio in normal MECs were defined as equivalent. Pairwise relationships among gene expression levels and clinicopathologic factors were tested by the non-parametric rank correlation method, Spearman's rho analysis (Table 2). Spearman rank correlations involving ER-LB assays, PgR-LB assays, S-phase fraction and DNA ploidy used raw values on continuous scales instead of simple status assessments. All of the analyses described above were performed using SAS version 8.2 from SAS Institute, Inc. (Cary, N.C.).

Results and Discussion

Statistical Considerations: The sample size in this study was modest: 38 tumors and 9 normal MEC preparations. However, statistically significant results observed with this modest sample size can indicate truly important relationships and differences. Notably, gene expression was accurately measured, even when at low levels, because of the use of real-time Q-PCR, thereby allowing much finer stratification of tissue samples than would have been possible by less quantitative methods (e.g., IHC or ligand-binding assays). Consequently, these more refined stratifications allowed improved statistical considerations given the modest sample size.

ERα exhibited significantly higher mRNA levels than the other evaluated nuclear receptors in approximately three-fourths of the tumors (FIG. 1A, compare FIG. 2A with FIG. 2B, FIG. 4, and FIG. 5). The median ERα mRNA level was 14-fold higher in breast carcinomas compared to normal MECs (Kruskal-Wallis ANOVA, P=0.002; FIG. 2A) and expressed at high or very high levels in 74% (28 of 38) of the breast tumors (FIG. 2A). These results exemplify the critical role ERα plays in the majority of breast cancers. The median ERα mRNA level was 34-fold greater in ER-LB-positive and 31-fold greater in PgR-LB-positive tumors relative to negative tumors (Kruskal-Wallis ANOVA, P<0.0001 and P=0.0001, respectively; FIG. 2A). Tumors that overexpressed ERα mRNA segregated with ER-LB and PgR-LB-positive status (Fisher's exact, P<0.0001 and P<0.0001, respectively; Table 1). Further, ERα mRNA levels strongly correlated with ER-LB ($p_s$=0.86, P<0.0001; Table 2) and PgR-LB protein levels ($p_s$=0.68, P<0.0001; Table 2) in the tumors as evaluated using the raw ligand-binding values over a continuous scale. These expected relationships validated the real-time Q-PCR assays and conformed well with established findings of others regarding both typical percentage of ER-LB-positive tumors and elevated levels of ERα in these tumors (67).

TABLE 1

Fisher's exact tests for association between aberrant gene expression and clinicopathological features

| mRNA Level | ER-LB | | | PgR-LB | | | S-phase Fraction | | | | DNA Ploidy | | |
|---|---|---|---|---|---|---|---|---|---|---|---|---|---|
| | Pos | Neg | P val | Pos | Neg | P val | Low | Int | High | P val | Di | Aneu | P val |
| ERα | | | | | | | | | | | | | |
| Normal | 2 | 8 | | 3 | 7 | | 5 | 1 | 4 | | 6 | 4 | |
| High | 17 | 2 | | 19 | 0 | | 11 | 3 | 4 | | 10 | 9 | |
| Very Hig | 9 | 0 | <0.0001 | 9 | 0 | <0.0001 | 5 | 1 | 3 | 0.88 | 4 | 5 | 0.91 |
| ERβ | | | | | | | | | | | | | |
| Low | 1 | 1 | | 2 | 0 | | 1 | 0 | 0 | | 2 | 0 | |
| Normal | 26 | 4 | | 27 | 3 | | 18 | 4 | 8 | | 15 | 15 | |
| High | 1 | 4 | | 1 | 4 | | 1 | 1 | 3 | | 2 | 3 | |
| Very Hig | 0 | 1 | 0.002 | 1 | 0 | 0.005 | 1 | 0 | 0 | 0.53 | 1 | 0 | 0.66 |
| EGFR* | | | | | | | | | | | | | |
| Typical | 27 | 5 | | 30 | 2 | | 18 | 5 | 9 | | 16 | 16 | |
| >Typica | 1 | 5 | 0.003 | 1 | 5 | 0.0002 | 3 | 0 | 2 | 1.00 | 4 | 2 | 0.66 |
| EGFR | | | | | | | | | | | | | |
| Very Low | 14 | 1 | | 15 | 0 | | 8 | 1 | 6 | | 7 | 8 | |
| Low | 14 | 7 | | 16 | 5 | | 12 | 4 | 4 | | 12 | 9 | |
| Normal | 0 | 2 | 0.012 | 0 | 2 | 0.003 | 1 | 0 | 1 | 0.51 | 1 | 1 | 0.86 |
| ErbB2 | | | | | | | | | | | | | |
| Normal | 25 | 7 | | 28 | 4 | | 18 | 4 | 9 | | 18 | 14 | |
| High | 3 | 1 | | 3 | 1 | | 3 | 0 | 1 | | 1 | 3 | |
| Very Hig | 0 | 2 | 0.11 | 0 | 2 | 0.029 | 0 | 1 | 1 | 0.35 | 1 | 1 | 0.65 |
| ErbB3 | | | | | | | | | | | | | |
| Low | 0 | 3 | | 1 | 2 | | 3 | 0 | 0 | | 3 | 0 | |
| Normal | 21 | 7 | | 23 | 5 | | 16 | 2 | 9 | | 15 | 13 | |
| High | 7 | 0 | 0.005 | 7 | 0 | 0.060 | 2 | 3 | 2 | 0.10 | 2 | 5 | 0.19 |
| ErbB4 | | | | | | | | | | | | | |
| Low | 1 | 4 | | 1 | 4 | | 2 | 1 | 2 | | 3 | 2 | |
| Normal | 15 | 6 | | 18 | 3 | | 12 | 2 | 6 | | 11 | 10 | |
| High | 12 | 0 | 0.002 | 12 | 0 | 0.002 | 7 | 2 | 3 | 0.86 | 6 | 6 | 1.00 |

TABLE 1-continued

Fisher's exact tests for association between aberrant gene expression and clinicopathological features

| mRNA Level | ER-LB Pos | ER-LB Neg | P val | PgR-LB Pos | PgR-LB Neg | P val | S-phase Fraction Low | S-phase Fraction Int | S-phase Fraction High | P val | DNA Ploidy Di | DNA Ploidy Aneu | P val |
|---|---|---|---|---|---|---|---|---|---|---|---|---|---|
| ERRα* | | | | | | | | | | | | | |
| <Typica | 1 | 0 | | 1 | 0 | | 1 | 0 | 1 | | 1 | 0 | |
| Typical | 26 | 5 | | 28 | 3 | | 18 | 4 | 7 | | 16 | 15 | |
| >Typica | 1 | 5 | 0.003 | 2 | 4 | 0.006 | 2 | 1 | 3 | 0.54 | 3 | 3 | 1.00 |
| ERRα | | | | | | | | | | | | | |
| Low | 3 | 3 | | 5 | 1 | | 4 | 0 | 1 | | 5 | 1 | |
| Normal | 25 | 7 | 0.31 | 26 | 6 | 1.00 | 17 | 5 | 10 | 0.66 | 15 | 17 | 0.18 |
| ERRβ | | | | | | | | | | | | | |
| Low | 5 | 0 | | 5 | 0 | | 1 | 1 | 2 | | 1 | 4 | |
| Normal | 22 | 8 | | 24 | 6 | | 18 | 4 | 7 | | 18 | 12 | |
| High | 1 | 1 | | 1 | 1 | | 1 | 0 | 1 | | 0 | 2 | |
| Very Hig | 0 | 1 | 0.12 | 1 | 0 | 0.38 | 1 | 0 | 0 | 0.61 | 1 | 0 | 0.069 |
| ERRγ | | | | | | | | | | | | | |
| Normal | 4 | 5 | | 5 | 4 | | 3 | 2 | 3 | | 4 | 5 | |
| High | 19 | 3 | | 20 | 2 | | 12 | 3 | 7 | | 10 | 12 | |
| Very Hig | 5 | 1 | 0.054 | 6 | 0 | 0.045 | 6 | 0 | 0 | 0.21 | 6 | 0 | 0.042 |

Pos (positive),
Neg (negative),
P val (P value),
Int (intermediate),
Di (diploid),
Aneu (aneuploid)
*(expression levels relative to other tumors, not MECs)

TABLE 2

Spearman's rank correlation coefficients (ρs) for pairwise comparisons in breast tumors and normal MECs

| | PgR-LB | S-phase | Ploidy | ERα | ERβ | EGFR | ErbB2 | ErbB3 | ErbB4 | ERRα | ERRβ | ERRγ | |
|---|---|---|---|---|---|---|---|---|---|---|---|---|---|
| ER-LB | 0.74* | −.070 | 0.09 | 0.86* | −0.11 | −0.76* | −0.01 | 0.17 | 0.53* | −0.23 | 0.11 | 0.19 | Breast |
| | <0.0001 | 0.68 | 0.59 | <0.0001 | 0.51 | <0.0001 | 0.97 | 0.30 | 0.001 | 0.16 | 0.51 | 0.27 | Tumors |
| | 39 | 38 | 39 | 38 | 38 | 38 | 38 | 38 | 38 | 38 | 38 | 37 | |
| PgR-LB | | −0.13 | 0.07 | 0.68* | −0.22 | −0.63* | 0.05 | 0.22 | 0.44* | −0.15 | 0.12 | 0.08 | |
| | | 0.43 | 0.68 | <0.0001 | 0.18 | <0.0001 | 0.76 | 0.19 | 0.006 | 0.39 | 0.47 | 0.63 | |
| | | 38 | 39 | 38 | 38 | 38 | 38 | 38 | 38 | 38 | 38 | 37 | |
| S-phase | | | 0.75* | −0.13 | 0.01 | −0.09 | 0.08 | 0.35* | −0.18 | 0.19 | −0.37* | −0.31 | |
| | | | <0.0001 | 0.43 | 0.95 | 0.60 | 0.63 | 0.034 | 0.29 | 0.26 | 0.026 | 0.07 | |
| | | | 39 | 37 | 37 | 37 | 37 | 37 | 37 | 37 | 37 | 36 | |
| Ploidy | | | | 0.06 | 0.05 | −0.24 | 0.13 | 0.19 | −0.04 | 0.19 | −0.19 | −0.27 | |
| | | | | 0.71 | 0.77 | 0.15 | 0.45 | 0.25 | 0.82 | 0.25 | 0.26 | 0.11 | |
| | | | | 38 | 38 | 38 | 38 | 38 | 38 | 38 | 38 | 37 | |
| ERα | | | | | −0.15 | −0.54 | 0.17 | 0.42* | 0.74* | −0.13 | 0.07 | 0.20 | |
| | | | | | 0.39 | 0.001 | 0.31 | 0.009 | <0.0001 | 0.44 | 0.66 | 0.24 | |
| | | | | | 38 | 38 | 38 | 38 | 38 | 38 | 38 | 37 | |
| ERβ | | | | | 0.27 | | 0.08 | 0.24 | −0.15 | −0.16 | 0.35* | 0.58* | −0.14 | |
| | | | | | 0.49 | | 0.64 | 0.14 | 0.36 | 0.34 | 0.032 | 0.0002 | 0.42 | |
| | | | | | 9 | | 38 | 38 | 38 | 38 | 38 | 38 | 37 | |
| EGFR | | | | 0.73* | 0.03 | | 0.27 | 0.09 | −0.30 | 0.19 | −0.13 | −0.17 | |
| | | | | 0.025 | 0.93 | | 0.19 | 0.57 | 0.07 | 0.25 | 0.44 | 0.31 | |
| | | | | 9 | 9 | | 38 | 38 | 38 | 38 | 38 | 37 | |
| ErbB2 | | | | 0.82* | 0.25 | 0.83* | | 0.54* | 0.04 | 0.45* | −0.10 | 0.10 | |
| | | | | 0.007 | 0.52 | 0.002 | | 0.0004 | 0.80 | 0.005 | 0.54 | 0.55 | |
| | | | | 9 | 9 | 9 | | 38 | 38 | 38 | 38 | 37 | |
| ErbB3 | | | | 0.52 | 0.15 | 0.48 | 0.70* | | 0.42* | 0.33* | −0.28 | 0.11 | |
| | | | | 0.15 | 0.70 | 0.19 | 0.036 | | 0.009 | 0.047 | 0.09 | 0.51 | |
| | | | | 9 | 9 | 9 | 9 | | 38 | 38 | 38 | 37 | |
| ErbB4 | | | | 0.35 | 0.27 | −0.15 | 0.20 | 0.60 | | −0.15 | −0.10 | 0.32* | |
| | | | | 0.36 | 0.49 | 0.70 | 0.61 | 0.09 | | 0.36 | 0.56 | 0.052 | |
| | | | | 9 | 9 | 9 | 9 | 9 | | 38 | 38 | 37 | |
| ERRα | | | | 0.70* | 0.33 | 0.90* | 0.93* | 0.57 | 0.05 | | 0.30 | 0.02 | |
| | | | | 0.036 | 0.38 | 0.0009 | 0.0002 | 0.11 | 0.90 | | 0.07 | 0.92 | |
| | | | | 9 | 9 | 9 | 9 | 9 | 9 | | 38 | 37 | |

TABLE 2-continued

Spearman's rank correlation coefficients ($\rho s$) for pairwise comparisons in breast tumors and normal MECs

| | PgR-LB | S-phase | Ploidy | ERα | ERβ | EGFR | ErbB2 | ErbB3 | ErbB4 | ERRα | ERRβ | ERRγ |
|---|---|---|---|---|---|---|---|---|---|---|---|---|
| ERRβ | | | | 0.23 | 0.27 | 0.50 | 0.58 | 0.28 | 0.00 | 0.77* | | −0.08 |
| | | | | 0.55 | 0.49 | 0.17 | 0.10 | 0.46 | 1.00 | 0.016 | | 0.62 |
| | | | | 9 | 9 | 9 | 9 | 9 | 9 | 9 | | 37 |
| ERRγ | | | | 0.48 | 0.33 | 0.14 | 0.64 | 0.81* | 0.76* | 0.38 | 0.17 | |
| | | | | 0.23 | 0.42 | 0.74 | 0.09 | 0.015 | 0.028 | 0.35 | 0.69 | |
| | | | | 8 | 8 | 8 | 8 | 8 | 8 | 8 | 8 | |

Normal MECs

*Spearman coefficient significance at P ≤ 0.05 (bolded)
Top ($\rho_s$), middle (P value), bottom (sample size)

ERβ mRNA Levels: ERβ mRNA levels were high or very high in 16% (6 of 38) of tumors and low in 5% (2 of 38) of tumors (FIG. 2B). The median level of ERβ mRNA expression was approximately 3.2-fold higher in PgR-LB-negative tumors compared to positive tumors (Kruskal-Wallis ANOVA, P=0.040; FIG. 2B). Dotzlaw et al. (68) have also reported increased ERβ expression in PgR-negative tumors. Also, tumors that overexpressed ERβ associated with ER-LB-negative and PgR-LB-negative status (Fisher's exact, P=0.002 and P=0.005, respectively; Table 1). Thus, increased ERβ levels inversely related with functional ERα status and may, therefore, have reflected improper estrogen responsiveness as has been suggested by others (7, 68, 69).

EGFR mRNA Levels: The median EGFR mRNA level was approximately 1/25$^{th}$ in breast tumors relative to normal MECs (Kruskal-Wallis ANOVA, P<0.0001; FIG. 3A), with 55% (21 of 38) of tumors showing low and 39% (15 of 38) showing very low expression (solid symbols, FIG. 3A). However, when compared within the tumors as a class, 16% (6 of 38) showed elevated or greater than typical levels of EGFR expression (triangles, FIG. 3A) in agreement with other reports (13). EGFR exhibited a strongly significant inverse relationship with ERα expression in breast tumors. The median EGFR mRNA level was approximately 7.4-fold higher in ER-LB-negative and 6.8-fold higher in PgR-LB-negative versus positive tumors (Kruskal-Wallis ANOVA, P=0.0002 and P=0.0004, respectively; FIG. 3A). Also, tumors exhibiting greater than typical EGFR levels associated with ER-LB-negative and PgR-LB-negative status (Fisher's exact, P=0.003 and P=0.0002, respectively; Table 1). Further, EGFR mRNA levels inversely correlated with ERα mRNA levels ($p_s$=−0.54, P=0.001; Table 2) as well as with ER-LB protein amounts ($p_s$=−0.76, P<0.0001; Table 2) and PgR-LB protein amounts ($p_s$=−0.63, P<0.0001; Table 2) over a continuous scale in tumors, while directly correlated with ERα mRNA levels in normal MECs ($p_s$=0.73, P=0.025; Table 2). These data indicate that EGFR and ERα were coregulated in the normal MECs, but, in accordance with previous reports (13), inversely regulated in the tumors, indicative of a negative feedback regulatory loop.

ErbB2 mRNA Levels: ErbB2 was the dominant transmembrane receptor as it was observed at markedly higher levels than the other ErbB members in every tissue subgroup (compare FIG. 3B with FIGS. 3A and 3C-3D). This finding is consistent with ErbB2 acting as the dominant heterodimerization subunit (11) and highlights its importance in mammary tissues. The median ErbB2 level showed a non-statistically significant 2.3-fold increase in expression in the breast tumors compared to the normal MECs (FIG. 3B). However, in agreement with reports of others (14, 17), ErbB2 expression was significantly increased in 16% (6 of 38) of tumors, with 11% displaying high and 5% displaying very high ErbB2 levels. The maximum level of ErbB2 expression was 18-fold higher in the tumors compared to the maximum level in the normal MECs. Overexpression of ErbB2 associated with PgR-LB-negative status (Fisher's exact, P=0.029; Table 1) and, thereby, inversely associated with ERα functionality in the tumors as has been previously demonstrated (14). On the other hand, ErbB2 mRNA levels directly correlated with both ERα mRNA levels ($p_s$=0.82, P=0.007; Table 2) and EGFR mRNA levels ($p_s$=0.83, P=0.002; Table 2) in the normal MECs. Thus, in a similar manner as EGFR, ErbB2 likely participated in similar functions along with ERα in the normal MECs, yet distinct functions from ERα in a subset of the tumors.

ErbB3 mRNA Levels: The median ErbB3 mRNA level showed a non-significant 2.0-fold increase in breast tumors compared to normal MECs (FIG. 3C). High expression of ErbB3 was observed in 18% (7 of 38) of the tumors, whereas low ErbB3 expression was observed in 8% (3 of 38) of the tumors. ErbB3 overexpression associated with ER-LB-positive tumor status (Fisher's exact, P=0.005; Table 1). Further, ErbB3 levels correlated with ERα mRNA levels in the tumors ($p_s$=0.42, P=0.009; Table 2), indicating that ErbB3 may have participated in ERα-mediated activities in this tissue type. A similar relationship between ErbB3 and ERα has been previously described (34). ErbB3 expression also correlated with ErbB2 expression in the tumors ($p_s$=0.54, P=0.0004; Table 2) and normal MECs ($p_s$=0.70, P=0.036; Table 2), consistent with a prior report (32) and suggesting that these ErbB members form heterodimers in both tissue types. Moreover, ErbB3 correlated with S-phase fraction ($p_s$=0.35, P=0.034; Table 2), an established clinical indicator of tumor aggressiveness. Hence, ErbB3 may have similar, yet distinct roles with both ErbB2 and ERα in tumor cell proliferation.

ErbB4 mRNA Levels: ErbB4 mRNA was present at high levels in 32% (12 of 38) of the tumors and at low levels in 13% (5 of 38) of them. Interestingly, ErbB4 mRNA levels were elevated 4.7-fold in the ER-LB-positive and 15-fold in the PgR-LB-positive tumors relative to the LB-negative tumors (Kruskal-Wallis ANOVA, P=0.001 and P=0.0002, respectively; FIG. 3D), and overexpression of ErbB4 associated with ER-LB-positive and PgR-LB-positive status (Fisher's exact, P=0.002 and P=0.002, respectively; Table 1). Furthermore, ErbB4 levels correlated with ERα mRNA levels ($p_s$=0.74, P<0.0001; Table 2) as well as with ER-LB ($p_s$=0.53, P=0.001; Table 2) and PgR-LB protein levels ($p_s$=0.44, P=0.006; Table 2) over a continuous scale in the tumors. Therefore, in accordance with a similar finding of Knowlden et al. (34), ErbB4 shared a strong relationship with ERα functionality in tumors. Levels of ErbB4 and ErbB3 correlated in tumors ($p_s$=0.42, P=0.009; Table 2), indicating that ErbB4 and ErbB3 likely shared some functions, potentially via the formation of heterodimers. Because the relationships observed between ErbB4 and ERα were stronger and more extensive than the ones observed between ErbB3 and ERα, the latter may have been the indirect result of heterodimerization between ErbB4 and ErbB3. These findings are consistent with reports showing that ErbB4 likely serves as a favorable biomarker (16, 34-36).

The median ERRα mRNA level in the breast tumors was non-significantly 44% of the median level observed in normal MECs, though 16% (6 of 38) of tumors did contain significantly lower levels of ERRα (solid symbols, FIG. 4A). However, when ERRα levels were compared within the tumor group, ERRα levels were significantly greater than typical in 16% (6 of 38) of the samples, while only 3% (1 of 38) of the samples showed significantly lower than typical levels (triangles, FIG. 4A). Quite importantly, most of these ERRα-elevated tumors were also ER-LB-negative and PgR-LB-negative (Fisher's exact, P=0.003 and P=0.006, respectively; Table 1), with the median ERRα mRNA level being significantly 2.5-fold higher in the PgR-LB-negative compared to PgR-LB-positive tumors (Kruskal-Wallis ANOVA, P=0.021, FIG. 4A). Thus, as with ERα, EGFR and ErbB2, higher levels of ERRα occurred in the absence of functional ERα in the tumors. ERRα levels correlated with ERβ levels in tumors ($p_s$=0.35, P=0.032; Table 2), and with ERα levels in normal MECs ($p_s$=0.70, P=0.036; Table 2). ERRα also correlated with ErbB3 in tumors ($p_s$=0.33, P=0.047; Table 2), and with EGFR in normal MECs ($p_s$=0.90, P=0.0009; Table 2). Additionally, ERRα displayed correlations with ErbB2 in both the tumors ($p_s$=0.45, P=0.005; Table 2) and normal MECs ($p_s$=0.93, P=0.0002; Table 2). Hence, while ERRα may have functioned together with ErbB2 in both normal and tumor mammary cells, it may have also acted together with ERα and EGFR in normal MECs, and with ERβ and ErbB3 apart from ERα in tumors. These correlations could be indicative of irregular estrogen responsiveness in the pathogenesis of breast cancer.

After ERα, ERRα was the next most abundant nuclear receptor, showing greater levels of expression than ERβ, ERRβ and ERRγ in every tissue subgroup (compare FIG. 4A with FIG. 2 and FIGS. 4B-4C). The distributions of ERα and ERRα expression were compared within the same tissue sample as paired variables by 1-way ANOVA with repeated measures (FIG. 5). ERα and ERRα were expressed at similar levels in normal MECs (P=0.14) and ER-LB-negative tumors (P=0.98), while ERα was more abundant in the ER-LB-positive (P<0.0001) and PgR-LB-positive groups (P<0.0001). Most importantly, ERRα levels were significantly greater than ERα levels in PgR-LB-negative tumors (P=0.030). ERRα was present at greater levels than ERα in 13% (5 of 38), at approximately equivalent levels in 11% (4 of 38), and at lower levels in 76% (29 of 38) of the tumors. Therefore, ERRα may have played a prominent role in ERE-dependent transcription in almost one-fourth of the breast tumors, while ERα may have played a greater physiological role in the remaining tumors.

ERRα's Potential Role in Breast Cancer: A primary conclusion from the above data is that ERRα showed a strong inverse relationship with ERα functionality in the tumors. Why might this be so? We hypothesize that ERRα functions in normal MECs as a modulator of the response to estrogen, competing with ERα for binding to EREs to achieve fine-tuned regulation of transcription. In support of this hypothesis, we have shown that ERα and ERRα directly compete for binding EREs, and that changes in the amount of ERRα modulates ERα-mediated ERE-dependent transcription (43). Misregulation can occur in tumors by several mechanisms. One common mechanism likely involves the overexpression of ERα, often accompanied by underexpression of ERRα relative to normal MECs, such that ERα outcompetes ERRα for binding to EREs. In this case, the modulatory effects of ERRα are largely lost. Alternatively, in ER-negative tumors or ones with high ERRα levels, ERRα becomes a major regulator of ERE-containing genes, acting constitutively since it functions independently of estrogen (37, 51).

Interestingly, ERRα has been shown to function actively as either a repressor (43) or activator (53, 59, 60) of transcription in mammary carcinoma cell lines in a cell type-dependent manner. The factors which determine ERRα's transcriptional activity have yet to be identified, but likely involve, in part, the ErbB2 signal transduction pathway. Here, we found ERRα mRNA abundance strongly correlated with ErbB2 abundance in both the breast tumors and normal MECs (Table 2), suggesting a functional relationship between these factors. Consistent with this correlation, ERRα has been shown to function as a transcriptional activator in SK-BR-3 mammary cells, cells in which the erbB2 locus has been amplified such that ErbB2 mRNA levels are 128-fold higher than in MCF-7 cells (76), while it functions as a transcriptional repressor in MCF-7 cells (43). ERRα has also been demonstrated to exist as a phosphoprotein in COS-7 cells, another cell line in which ERRα activates transcription (48). Moreover, we have recently found that ERRα can serve as a substrate for activated MAPK in vitro. Thus, ERRα and ErbB2 likely share a functional relationship through ErbB2-mediated modulation of ERRα's phosphorylation status. Combining these observations, we propose the following hypothesis: in cells containing low ErbB2 levels, ERRα down-modulates ERα-regulated ERE-dependent transcription; in cells containing high ErbB2 levels, ERRα constitutively activates transcription independent of ERα. A major prediction of this hypothesis is that tumors containing high levels of both ErbB2 and ERRα will not likely respond to antiestrogen therapy. This hypothesis also provides one of multiple mechanisms to explain ErbB2's relationship with tamoxifen resistance (18, 21, 22) and suggests that ERRα's phosphorylation status may have predictive value in assessing the effectiveness of therapeutic agents such as Herceptin which are directed against ErbB2. It also implicates ERRα itself as another likely efficacious target for therapy.

ERRβ mRNA was increased in 8% (3 of 38) of tumors (FIG. 4B) and decreased in 3% (1 of 38) of tumors. Aberrant ERRβ expression was not associated with any of the clinical biomarkers, though too few tumors contained aberrant ERRβ amounts for strong statistical testing. Indicative of roles with other genes, ERRβ levels correlated with ERRα levels in normal MECs ($p_s$=0.77, P=0.016; Table 2), and with ERβ in the tumors ($p_s$=0.58, P=0.0002; Table 2). The potential role of ERRβ in breast cancer may lie in its correlation with ERβ, which has been associated with indicators of high tumor aggressiveness (7, 68, 69). Curiously, ERRβ levels inversely correlated with S-phase fraction ($p_s$=−0.37, P=0.026; Table 2), perhaps suggesting that greater ERRβ levels inhibit cellular proliferation or, possibly, promote cellular differentiation. The importance for ERRβ in differentiation has been demonstrated by genetic ablation of this locus in mice, producing a severe defect in placental development that leads to embryonic lethality (77). However, the predictive value of ERRβ status remains unclear. It should be noted that ERRβ mRNA levels were quite low (FIG. 4B), indicating the prognostic potential of ERRβ is not promising. However, ERRβ mRNA levels were also quite low compared to ERα (FIG. 1 and FIG. 2), yet allow accumulation of ERβ protein to levels clearly detectable by IHC and participation in biologically significant roles in breast cancer (6, 7).

The median ERRγ mRNA level was significantly elevated 3.9-fold in breast tumors relative to normal MECs (Kruskal-Wallis ANOVA, P=0.001; FIG. 4C). Moreover, ERRγ mRNA was overexpressed in approximately three-fourths of the tumors, with high levels in 59% (22 of 37) and very high levels in an additional 16% (6 of 37) (FIG. 4C). These findings indicate that ERRγ was involved in the development of breast cancer. The median ERRγ mRNA level was not significantly different among the ER-LB or PgR-LB tumor subgroups. Nonetheless, tumors that overexpressed ERRγ were associated with ER-LB-positive and PgR-LB-positive status (Fisher's exact, P=0.054 and P=0.045, respectively; Table 1). Thus, tumors that overexpressed ERRγ were also frequently steroid receptor-positive, similar to tumors overexpressing ErbB3 or ErbB4. Hence, increased ERRγ levels reflect hormonal sensitivity. ERRγ levels correlated with ErbB4 levels in both the tumors ($p_s$ =0.32, P=0.052; Table 2) and normal MECs ($p_s$=0.76, P=0.028; Table 2), as well as with ErbB3 levels in normal MECs ($p_s$=0.81, P=0.015; Table 2). As discussed above, ErbB4 overexpression likely indicates a preferable clinical outcome; likewise, ERRγ overexpression can also indicate a more positive outcome. Interestingly, the median ERRγ level was 2.0-fold higher in the less aggressive-in-nature diploid tumors (157 copies/ng cDNA) compared to the aneuploid tumors (79 copies/ng cDNA; Kruskal-Wallis ANOVA, P=0.033; data not shown), and the tumors that overexpressed ERRγ associated with diploid status (Fisher's exact, P=0.042; Table 1). Collectively, these findings indicate that ERRγ can serve as a marker of favorable clinical course. Further, in light of the studies that demonstrated ERRγ binds 4-hydroxytamoxifen as an antagonist (46, 52, 54), ERRγ-overexpressing tumors can help identify a subset of patients that would benefit from this treatment.

Conclusions

The study described here represents an investigation into the potential utility of ERRs as biomarkers in human breast cancer. It was found that ERRα mRNA is a major species (FIGS. 1 and 4), being expressed at levels greater than or similar to ERα in 24% of the tumors (FIG. 5), with tumors containing the highest levels of ERRα being associated with a steroid receptor-negative status (Table 1, FIG. 4A) and, therefore, hormonal insensitivity. ERRα levels also directly correlated with levels of ErbB2 (Table 2), a marker of aggressive tumor behavior (14). Thus, ERRα may be an important unfavorable marker in a significant proportion of breast cancer patients. Additionally, ERRα status may indicate the effectiveness of ErbB2-based therapeutics, with ERRα itself being a candidate therapeutic target, especially for tumors lacking functional ERα. ERRγ was overexpressed in 75% of the tumors (FIG. 4C), indicating a role for this transcription factor in the pathogenesis of breast cancer. However, unlike ERRα, ERRγ overexpression associated with the presence of functional ERα (Table 1) and, hence, hormonal sensitivity. Further, ERRγ levels correlated with levels of ErbB4 (Table 2), a likely positive indicator of clinical outcome (16, 34-36), as well as with less aggressive diploid tumors (Table 1). Therefore, ERRγ is a favorable marker of clinical course. Moreover, since 4-hydroxytamoxifen has been found to antagonize ERRγ (46, 52, 54), selection of patients for treatment with this SERM may be improved by knowledge of ERRγ status. In summary, the results presented here demonstrate that the status of ERRα and ERRγ indicate clinical outcomes and sensitivity to hormonal therapy.

The present invention is not intended to be limited to the foregoing examples, but encompasses all such modifications and variations as come within the scope of the appended claims.

REFERENCES

1. Edwards, B. K., Howe, H. L., Ries, L. A., Thun, M. J., Rosenberg, H. M., Yancik, R., Wingo, P. A., Jemal, A., and Feigal, E. G. Annual report to the nation on the status of cancer, 1973 through 1999, featuring implications of age and aging on U.S. cancer burden. Cancer, 94: 2766-2792, 2002.
2. Nuclear Receptors Nomenclature Committee. A unified nomenclature system for the nuclear receptor superfamily. Cell, Vol. 97, pp. 161-163, 1999.
3. Sanchez, R., Nguyen, D., Rocha, W., White, J. H., and Mader, S. Diversity in the mechanisms of gene regulation by estrogen receptors. Bioessays, 24: 244-254, 2002.
4. Russo, J., Hu, Y. F., Yang, X., and Russo, I. H. Developmental, cellular, and molecular basis of human breast cancer. J Natl Cancer Inst Monogr, 27: 17-37, 2000.
5. Clark, G. M. and McGuire, W. L. Prognostic factors in primary breast cancer. Breast Cancer Res Treat, 3: S69-72, 1983.
6. Jarvinen, T. A., Pelto-Huikko, M., Holli, K., and Isola, J. Estrogen receptor beta is coexpressed with ERalpha and PR and associated with nodal status, grade, and proliferation rate in breast cancer. Am J Pathol, 156: 29-35, 2000.
7. Jensen, E. V., Cheng, G., Palmieri, C., Saji, S., Makela, S., Van Noorden, S., Wahlstrom, T., Warner, M., Coombes, R. C., and Gustafsson, J. A. Estrogen receptors and proliferation markers in primary and recurrent breast cancer. Proc Natl Acad Sci USA, 98: 15197-15202, 2001.
8. Stem, D. F. Tyrosine kinase signalling in breast cancer: ErbB family receptor tyrosine kinases. Breast Cancer Res, 2: 176-183, 2000.
9. Olayioye, M. A. Update on HER-2 as a target for cancer therapy: Intracellular signaling pathways of ErbB2/HER-2 and family members. Breast Cancer Res, 3: 385-389, 2001.
10. Klapper, L. N., Glathe, S., Vaisman, N., Hynes, N. E., Andrews, G. C., Sela, M., and Yarden, Y. The ErbB-2/HER2 oncoprotein of human carcinomas may function solely as a shared coreceptor for multiple stroma-derived growth factors. Proc Natl Acad Sci USA, 96: 4995-5000., 1999.
11. Klapper, L. N., Kirschbaum, M. H., Sela, M., and Yarden, Y. Biochemical and clinical implications of the ErbB/HER signaling network of growth factor receptors. Adv Cancer Res, 77: 25-79, 2000.
12. Guy, P. M., Platko, J. V., Cantley, L. C., Cerione, R. A., and Carraway, K. L., 3rd Insect cell-expressed p180erbB3 possesses an impaired tyrosine kinase activity. Proc Natl Acad Sci USA, 91: 8132-8136., 1994.
13. Klijn, J. G., Bems, P. M., Schmitz, P. I., and Foekens, J. A. The clinical significance of epidermal growth factor receptor (EGF-R) in human breast cancer: a review on 5232 patients. Endocr Rev, 13: 3-17, 1992.
14. Hynes, N. E. and Stern, D. F. The biology of erbB-2/neu/HER-2 and its role in cancer. Biochim Biophys Acta, 1198: 165-184, 1994.
15. Torregrosa, D., Bolufer, P., Lluch, A., Lopez, J. A., Barragan, E., Ruiz, A., Guillem, V., Munarriz, B., and Garcia Conde, J. Prognostic significance of c-erbB-2/neu amplification and epidermal growth factor receptor (EGFR) in primary breast cancer and their relation to estradiol receptor (ER) status. Clin Chim Acta, 262: 99-119., 1997.
16. Suo, Z., Risberg, B., Kalsson, M. G., Willman, K., Tierens, A., Skovlund, E., and Nesland, J. M. EGFR family expression in breast carcinomas. c-erbB-2 and c-erbB-4 receptors have different effects on survival. J Pathol, 196: 17-25, 2002.
17. Slamon, D. J., Clark, G. M., Wong, S. G., Levin, W. J., Ullrich, A., and McGuire, W. L. Human breast cancer: correlation of relapse and survival with amplification of the HER-2/neu oncogene. Science, 235: 177-182., 1987.
18. Wright, C., Nicholson, S., Angus, B., Sainsbury, J. R., Farndon, J., Cairns, J., Harris, A. L., and Horne, C. H. Relationship between c-erbB-2 protein product expression and response to endocrine therapy in advanced breast cancer. Br J Cancer, 65: 118-121, 1992.
19. Borg, A., Baldetorp, B., Ferno, M., Killander, D., Olsson, H., Ryden, S., and Sigurdsson, H. ERBB2 amplification is associated with tamoxifen resistance in steroid-receptor positive breast cancer. Cancer Lett, 81: 137-144, 1994.
20. Newby, J. C., Johnston, S. R., Smith, I. E., and Dowsett, M. Expression of epidermal growth factor receptor and c-erbB2 during the development of tamoxifen resistance in human breast cancer. Clin Cancer Res, 3: 1643-1651, 1997.
21. Houston, S. J., Plunkett, T. A., Barnes, D. M., Smith, P., Rubens, R. D., and Miles, D. W. Overexpression of c-erbB2 is an independent marker of resistance to endocrine therapy in advanced breast cancer. Br J Cancer, 79: 1220-1226, 1999.
22. Dowsett, M., Harper-Wynne, C., Boeddinghaus, I., Salter, J., Hills, M., Dixon, M., Ebbs, S., Gui, G., Sacks, N., and Smith, I. HER-2 amplification impedes the antiproliferative effects of hormone therapy in estrogen receptor-positive primary breast cancer. Cancer Res, 61: 8452-8458, 2001.
23. Lipton, A., Ali, S. M., Leitzel, K., Demers, L., Chinchilli, V., Engle, L., Harvey, H. A., Brady, C., Nalin, C. M., Dugan, M., Carney, W., and Allard, J. Elevated serum Her-2/neu level predicts decreased response to hormone therapy in metastatic breast cancer. J Clin Oncol, 20: 1467-1472., 2002.
24. Elledge, R. M., Green, S., Ciocca, D., Pugh, R., Allred, D. C., Clark, G. M., Hill, J., Ravdin, P., O'Sullivan, J., Martino, S., and Osborne, C. K. HER-2 expression and response to tamoxifen in estrogen receptor-positive breast cancer: a Southwest Oncology Group Study. Clin Cancer Res, 4: 7-12, 1998.
25. Berry, D. A., Muss, H. B., Thor, A. D., Dressler, L., Liu, E. T., Broadwater, G., Budman, D. R., Henderson, I. C., Barcos, M., Hayes, D., and Norton, L. HER-2/neu and p53 expression versus tamoxifen resistance in estrogen receptor-positive, node-positive breast cancer. J Clin Oncol, 18: 3471-3479., 2000.
26. Sliwkowski, M. X., Lofgren, J. A., Lewis, G. D., Hotaling, T. E., Fendly, B. M., and Fox, J. A. Nonclinical studies addressing the mechanism of action of trastuzumab (Herceptin). Semin Oncol, 26: 60-70, 1999.
27. Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., Shak, S., Stewart, S. J., and Press, M. Efficacy and safety of trastuzumab as a single agent in first-line treatment of HER2-overexpressing metastatic breast cancer. J Clin Oncol, 20: 719-726, 2002.
28. Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. Use of chemotherapy plus a monoclonal antibody against HER2 for metastatic breast cancer that overexpresses HER2. N Engl J Med, 344: 783-792, 2001.
29. Esteva, F. J., Valero, V., Booser, D., Guerra, L. T., Murray, J. L., Pusztai, L., Cristofanilli, M., Arun, B., Esmaeli, B., Fritsche, H. A., Sneige, N., Smith, T. L., and Hortobagyi, G. N. Phase II study of weekly docetaxel and trastuzumab for patients with HER-2-overexpressing metastatic breast cancer. J Clin Oncol, 20: 1800-1808., 2002.
30. Moulder, S. L., Yakes, F. M., Muthuswamy, S. K., Bianco, R., Simpson, J. F., and Arteaga, C. L. Epidermal growth factor receptor (HER1) tyrosine kinase inhibitor ZD 1839 (Iressa) inhibits HER2/neu (erbB2)-overexpressing breast cancer cells in vitro and in vivo. Cancer Res, 61: 8887-8895, 2001.
31. Normanno, N., Campiglio, M., De Luca, A., Somenzi, G., Maiello, M., Ciardiello, F., Gianni, L., Salomon, D. S., and Menard, S. Cooperative inhibitory effect of ZD1839 (Iressa) in combination with trastuzumab (Herceptin) on human breast cancer cell growth. Ann Oncol, 13: 65-72., 2002.
32. Gasparini, G., Gullick, W. J., Maluta, S., Dalla Palma, P., Caffo, O., Leonardi, E., Boracchi, P., Pozza, F., Lemoine, N. R., and Bevilacqua, P. c-erbB-3 and c-erbB-2 protein expression in node-negative breast carcinoma—an immunocytochemical study. Eur J Cancer, 30A: 16-22, 1994.
33. Lemoine, N. R., Barnes, D. M., Hollywood, D. P., Hughes, C. M., Smith, P., Dublin, E., Prigent, S. A., Gullick, W. J., and Hurst, H. C. Expression of the ERBB3 gene product in breast cancer. Br J Cancer, 66: 1116-1121, 1992.
34. Knowlden, J. M., Gee, J. M., Seery, L. T., Farrow, L., Gullick, W. J., Ellis, I. O., Blarney, R. W., Robertson, J. F., and Nicholson, R. I. c-erbB3 and c-erbB4 expression is a feature of the endocrine responsive phenotype in clinical breast cancer. Oncogene, 17: 1949-1957, 1998.
35. Bacus, S. S., Chin, D., Yarden, Y., Zelnick, C. R., and Stern, D. F. Type 1 receptor tyrosine kinases are differentially phosphorylated in mammary carcinoma and differentially associated with steroid receptors. Am J Pathol, 148: 549-558, 1996.
36. Kew, T. Y., Bell, J. A., Pinder, S. E., Denley, H., Srinivasan, R., Gullick, W. J., Nicholson, R. I., Blamey, R. W., and Ellis, I. O. c-erbB-4 protein expression in human breast cancer. Br J Cancer, 82: 1163-1170, 2000.
37. Giguere, V., Yang, N., Segui, P., and Evans, R. M. Identification of a new class of steroid hormone receptors. Nature, 331: 91-94, 1988.
38. Shi, H., Shigeta, H., Yang, N., Fu, K., O'Brian, G., and Teng, C. T. Human estrogen receptor-like 1 (ESRL1) gene: genomic organization, chromosomal localization, and promoter characterization. Genomics, 44: 52-60, 1997.

39. Johnston, S. D., Liu, X., Zuo, F., Eisenbraun, T. L., Wiley, S. R., Kraus, R. J., and Mertz, J. E. Estrogen-related receptor alpha 1 functionally binds as a monomer to extended half-site sequences including ones contained within estrogen-response elements. Mol Endocrinol, 11: 342-352, 1997.

40. Chen, F., Zhang, Q., McDonald, T., Davidoff, M. J., Bailey, W., Bai, C., Liu, Q., and Caskey, C. T. Identification of two hERR2-related novel nuclear receptors utilizing bioinformatics and inverse PCR. Gene, 228: 101-109, 1999.

41. Eudy, J. D., Yao, S., Weston, M. D., Ma-Edmonds, M., Talmadge, C. B., Cheng, J. J., Kimberling, W. J., and Sumegi, J. Isolation of a gene encoding a novel member of the nuclear receptor superfamily from the critical region of Usher syndrome type IIa at 1q41. Genomics, 50: 382-384, 1998.

42. Heard, D. J., Norby, P. L., Holloway, J., and Vissing, H. Human ERRgamma, a third member of the estrogen receptor-related receptor (ERR) subfamily of orphan nuclear receptors: tissue-specific isoforms are expressed during development and in the adult. Mol Endocrinol, 14: 382-392, 2000.

43. Kraus, R. J., Ariazi, E. A., Farrell, M. L., and Mertz, J. E. Estrogen-related receptor alpha 1 actively antagonizes estrogen receptor-regulated transcription in MCF-7 mammary cells. J Biol Chem, Vol. 277, pp. 24826-24834, 2002.

44. Vanacker, J. M., Pettersson, K., Gustafsson, J. A., and Laudet, V. Transcriptional targets shared by estrogen receptor-related receptors (ERRs) and estrogen receptor (ER) alpha, but not by ERbeta. EMBO J, 18: 4270-4279, 1999.

45. Hong, H., Yang, L., and Stallcup, M. R. Hormone-independent transcriptional activation and coactivator binding by novel orphan nuclear receptor ERR3. J Biol Chem, 274: 22618-22626, 1999.

46. Coward, P., Lee, D., Hull, M. V., and Lehmann, J. M. 4-Hydroxytamoxifen binds to and deactivates the estrogen-related receptor gamma. Proc Natl Acad Sci USA, 98: 8880-8884, 2001.

47. Bonnelye, E., Vanacker, J. M., Spruyt, N., Alric, S., Fournier, B., Desbiens, X., and Laudet, V. Expression of the estrogen-related receptor 1 (ERR-1) orphan receptor during mouse development. Mech Dev, 65: 71-85, 1997.

48. Sladek, R., Bader, J. A., and Giguere, V. The orphan nuclear receptor estrogen-related receptor alpha is a transcriptional regulator of the human medium-chain acyl coenzyme A dehydrogenase gene. Mol Cell Biol, 17: 5400-5409, 1997.

49. Vanacker, J. M., Bonnelye, E., Chopin-Delannoy, S., Delmarre, C., Cavailles, V., and Laudet, V. Transcriptional activities of the orphan nuclear receptor ERR alpha (estrogen receptor-related receptor-alpha). Mol Endocrinol, 13: 764-773, 1999.

50. Xie, W., Hong, H., Yang, N. N., Lin, R. J., Simon, C. M., Stallcup, M. R., and Evans, R. M. Constitutive activation of transcription and binding of coactivator by estrogen-related receptors 1 and 2. Mol Endocrinol, 13: 2151-2162, 1999.

51. Tremblay, G. B., Kunath, T., Bergeron, D., Lapointe, L., Champigny, C., Bader, J. A., Rossant, J., and Giguere, V. Diethylstilbestrol regulates trophoblast stem cell differentiation as a ligand of orphan nuclear receptor ERR beta. Genes Dev, 15: 833-838, 2001.

52. Greschik, H., Wurtz, J. M., Sanglier, S., Bourguet, W., van Dorsselaer, A., Moras, D., and Renaud, J. P. Structural and functional evidence for ligand-independent transcriptional activation by the estrogen-related receptor 3. Mol Cell, 9: 303-313, 2002.

53. Chen, S., Zhou, D., Yang, C., and Sherman, M. Molecular basis for the constitutive activity of estrogen related receptor alpha-1. J Biol Chem, 276: 28465-28470, 2001.

54. Tremblay, G. B., Bergeron, D., and Giguere, V. 4-Hydroxytamoxifen is an isoform-specific inhibitor of orphan estrogen-receptor-related (ERR) nuclear receptors beta and gamma. Endocrinology, 142: 4572-4575, 2001.

55. Lu, D., Kiriyama, Y., Lee, K. Y., and Giguere, V. Transcriptional regulation of the estrogen-inducible pS2 breast cancer marker gene by the ERR family of orphan nuclear receptors. Cancer Res, 61: 6755-6761, 2001.

56. Yang, N., Shigeta, H., Shi, H., and Teng, C. T. Estrogen-related receptor, hERR1, modulates estrogen receptor-mediated response of human lactoferrin gene promoter. J Biol Chem, 271: 5795-5804, 1996.

57. Bonnelye, E., Vanacker, J. M., Dittmar, T., Begue, A., Desbiens, X., Denhardt, D. T., Aubin, J. E., Laudet, V., and Fournier, B. The ERR-1 orphan receptor is a transcriptional activator expressed during bone development. Mol Endocrinol, 11: 905-916, 1997.

58. Vanacker, J. M., Delmarre, C., Guo, X., and Laudet, V. Activation of the osteopontin promoter by the orphan nuclear receptor estrogen receptor related alpha. Cell Growth Differ, 9: 1007-1014, 1998.

59. Yang, C., Zhou, D., and Chen, S. Modulation of aromatase expression in the breast tissue by ERR alpha-1 orphan receptor. Cancer Res, 58: 5695-5700, 1998.

60. Yang, C. and Chen, S. Two organochlorine pesticides, toxaphene and chlordane, are antagonists for estrogen-related receptor alpha-1 orphan receptor. Cancer Res, 59: 4519-4524, 1999.

61. Zhang, Z. and Teng, C. T. Estrogen receptor-related receptor alpha 1 interacts with coactivator and constitutively activates the estrogen response elements of the human lactoferrin gene. J Biol Chem, 275: 20837-20846, 2000.

62. Zhang, Z. and Teng, C. T. Estrogen receptor alpha and estrogen receptor-related receptor alpha1 compete for binding and coactivator. Mol Cell Endocrinol, 172: 223-233., 2001.

63. Bustin, S. A. Absolute quantification of mRNA using real-time reverse transcription polymerase chain reaction assays. J Mol Endocrinol, Vol. 25, pp. 169-193, 2000.

64. Dressler, L. G., Seamer, L. C., Owens, M. A., Clark, G. M., and McGuire, W. L. DNA flow cytometry and prognostic factors in 1331 frozen breast cancer specimens. Cancer, 61: 420-427, 1988.

65. Wenger, C. R., Beardslee, S., Owens, M. A., Pounds, G., Oldaker, T., Vendely, P., Pandian, M. R., Harrington, D., Clark, G. M., and McGuire, W. L. DNA ploidy, S-phase, and steroid receptors in more than 127,000 breast cancer patients. Breast Cancer Res Treat, 28: 9-20, 1993.

66. Eisen, M. B., Spellman, P. T., Brown, P. O., and Botstein, D. Cluster analysis and display of genome-wide expression patterns. Proc Natl Acad Sci USA, 95: 14863-14868, 1998.

67. Clark, G. M., McGuire, W. L., Hubay, C. A., Pearson, O. H., and Carter, A. C. The importance of estrogen and progesterone receptor in primary breast cancer. Prog Clin Biol Res 183-190, 1983.

68. Dotzlaw, H., Leygue, E., Watson, P. H., and Murphy, L. C. Estrogen receptor-beta messenger RNA expression in human breast tumor biopsies: relationship to steroid receptor status and regulation by progestins. Cancer Res, 59: 529-532, 1999.
69. Speirs, V. and Kerin, M. J. Prognostic significance of oestrogen receptor beta in breast cancer. Br J Surg, 87: 405-409, 2000.
70. Brandt, B. H., Roetger, A., Dittmar, T., Nikolai, G., Seeling, M., Merschjann, A., Nofer, J. R., Dehmer-Moller, G., Junker, R., Assmann, G., and Zaenker, K. S. c-erbB-2/EGFR as dominant heterodimerization partners determine a motogenic phenotype in human breast cancer cells. Faseb J, 13: 1939-1949., 1999.
71. Yarden, R. I., Lauber, A. H., El-Ashry, D., and Chrysogelos, S. A. Bimodal regulation of epidermal growth factor receptor by estrogen in breast cancer cells. Endocrinology, 137: 2739-2747, 1996.
72. Chrysogelos, S. A., Yarden, R. I., Lauber, A. H., and Murphy, J. M. Mechanisms of EGF receptor regulation in breast cancer cells. Breast Cancer Res Treat, 31: 227-236, 1994.
73. Miller, D. L., el-Ashry, D., Cheville, A. L., Liu, Y., McLeskey, S. W., and Kern, F. G. Emergence of MCF-7 cells overexpressing a transfected epidermal growth factor receptor (EGFR) under estrogen-depleted conditions: evidence for a role of EGFR in breast cancer growth and progression. Cell Growth Differ, 5: 1263-1274., 1994.
74. Nicholson, S., Wright, C., Sainsbury, J. R., Halcrow, P., Kelly, P., Angus, B., Farndon, J. R., and Harris, A. L. Epidermal growth factor receptor (EGFr) as a marker for poor prognosis in node-negative breast cancer patients: neu and tamoxifen failure. J Steroid Biochem Mol Biol, 37: 811-814, 1990.
75. Nicholson, S., Halcrow, P., Sainsbury, J. R., Angus, B., Chambers, P., Farndon, J. R., and Harris, A. L. Epidermal growth factor receptor (EGFr) status associated with failure of primary endocrine therapy in elderly postmenopausal patients with breast cancer. Br J Cancer, 58: 810-814., 1988.
76. Kraus, M. H., Popescu, N. C., Amsbaugh, S. C., and King, C. R. Overexpression of the EGF receptor-related proto-oncogene erbB-2 in human mammary tumor cell lines by different molecular mechanisms. Embo J, 6: 605-610, 1987.
77. Luo, J., Sladek, R., Bader, J. A., Matthyssen, A., Rossant, J., and Giguere, V. Placental abnormalities in mouse embryos lacking the orphan nuclear receptor ERR-beta. Nature, 388: 778-782, 1997.
78. Speirs, V., Malone, C., Walton, D. S., Kerin, M. J., and Atkin, S. L. Increased expression of estrogen receptor beta mRNA in tamoxifen-resistant breast cancer patients. Cancer Res, 59: 5421-5424., 1999.

We claim:

1. A method for determining prognosis of breast cancer comprising the steps of:
   determining the mRNA level of estrogen-related receptor γ (ERRγ) in breast cancer cells of a breast cancer patient; and
   comparing the ERRγ mRNA level of the patient to a median ERRγ mRNA level of a population of at least twenty-five breast cancer patients as expressed in their breast cancer cells wherein breast cancer patients with an ERRγ mRNA level higher than the median level have good prognosis and breast cancer patients with an ERRγ mRNA level lower than the median level have poor prognosis in that breast cancer patients with an ERRγ mRNA level higher than the median level are more likely to respond to hormonal blockade therapy than breast cancer patients with an ERRγ mRNA level lower than the median level.

2. A method for identifying breast cancer patients that may benefit from tamoxifen comprising the steps of:
   determining the ERRγ mRNA level in breast cancer cells of a breast cancer patient; and
   comparing the ERRγ mRNA level of the patient to a median ERRγ mRNA level of a population of at least twenty-five breast cancer patients as expressed in their breast cancer cells wherein breast cancer patients with an ERRγ mRNA level higher than the median level are more likely to respond to tamoxifen than breast cancer patients with an ERRγ mRNA level lower than the median level.

3. A method for determining whether a breast cancer patient is likely to respond to hormonal blockade therapy comprising the steps of:
   determining the ERRγ mRNA level and estrogen receptor (ER) α status in breast cancer cells of the patient; and
   comparing the ERRγ mRNA level of the patient to a median ERRγ mRNA level of a population of at least twenty-five breast cancer patients as expressed in their breast cancer cells, wherein breast cancer patients with breast cancer cells that are ERα positive and express ERRγ at a level higher than the median level are more likely to respond to hormonal blockade therapy than breast cancer patients with breast cancer cells that are ERα positive and express ERRγ at a lower level than the median level.

4. A method for diagnosing breast cancer comprising the steps of:
   measuring the ERRγ mRNA level in the cells of a breast region suspected of being cancerous in a human subject; and
   comparing the mRNA level to that of normal breast epithelial cells wherein a higher ERRγ mRNA level than that of normal breast epithelial cells indicates breast cancer.

5. The method of claim 4, wherein the ERRγ mRNA level of normal breast epithelial cells is the ERRγ mRNA level of normal breast epithelial cells of the human subject obtained during a breast cancer-free period.

6. The method of claim 4, wherein the ERRγ mRNA level of normal breast epithelial cells is the ERRγ mRNA level of the non-cancerous breast epithelial cells of the human subject obtained from a disease-free region of the breast.

* * * * *